(12) United States Patent
Guerrero Navarro

(10) Patent No.: US 11,371,998 B2
(45) Date of Patent: Jun. 28, 2022

(54) DEVICES AND KITS TO IMPROVE REDUCTION OR LABELING OF CARBOHYDRATES

(71) Applicant: Agilent Technologies, Inc., Santa Clara, CA (US)

(72) Inventor: Andres Guerrero Navarro, Pamplona (ES)

(73) Assignee: Agilent Technologies, Inc., Santa Clara, CA (US)

( * ) Notice: Subject to any disclaimer, the term of this patent is extended or adjusted under 35 U.S.C. 154(b) by 209 days.

(21) Appl. No.: 16/495,024

(22) Filed: Sep. 17, 2019

(65) Prior Publication Data

US 2020/0346214 A1 Nov. 5, 2020

Related U.S. Application Data

(63) Continuation of application No. PCT/US2018/023875, filed on Mar. 22, 2018.
(Continued)

(51) Int. Cl.
| | | |
|---|---|---|
| *G01N 33/58* | (2006.01) | |
| *C07H 1/00* | (2006.01) | |
| *C07H 3/06* | (2006.01) | |
| *G01N 21/64* | (2006.01) | |

(Continued)

(52) U.S. Cl.
CPC ............ *G01N 33/582* (2013.01); *B01L 3/508* (2013.01); *B01L 3/5082* (2013.01); *B01L 3/5085* (2013.01); *B01L 3/502761* (2013.01); *B01L 3/523* (2013.01); *B01L 3/56* (2013.01); *C07H 1/00* (2013.01); *C07H 3/06* (2013.01);
(Continued)

(58) Field of Classification Search
CPC ...... G01N 33/582; G01N 1/34; G01N 1/4077; G01N 21/643; G01N 21/6452; G01N 2001/4088; B01L 3/502761; B01L 3/508; B01L 3/5082; B01L 3/5085; B01L 3/523; B01L 3/56; B01L 2200/16; B01L 2300/041; B01L 2300/069; B01L 2300/0845;
(Continued)

(56) References Cited

U.S. PATENT DOCUMENTS

| | | |
|---|---|---|
| 2002/0051971 A1 | 5/2002 | Stuelpnagel |
| 2008/0227092 A1 | 9/2008 | Lohse |

(Continued)

FOREIGN PATENT DOCUMENTS

| | | |
|---|---|---|
| EP | 2282209 A1 | 2/2011 |
| WO | WO2012037407 A1 | 3/2012 |

(Continued)

OTHER PUBLICATIONS

Ikegami et al., "Highly efficient analysis of underivatized carbohydrates using monolithic-silica-based capillary hydrophilic . . . " Anal Bioanal Chem, 2008, 391(7):2533-2542.
(Continued)

*Primary Examiner* — Jennifer Wecker
*Assistant Examiner* — Kathryn Elizabeth Limbaugh
(74) *Attorney, Agent, or Firm* — Laurence J. Hyman; Hyman IP Law

(57) ABSTRACT

The present invention provides methods, devices, and kits to improve procedures for reducing carbohydrates, such as glycans released from glycoconjugates, or for labeling carbohydrates by reductive amination.

34 Claims, 1 Drawing Sheet

Related U.S. Application Data

(60) Provisional application No. 62/644,460, filed on Mar. 17, 2018, provisional application No. 62/636,815, filed on Feb. 28, 2018, provisional application No. 62/475,815, filed on Mar. 23, 2017.

(51) Int. Cl.
*B01L 3/00* (2006.01)
*G01N 1/34* (2006.01)
*G01N 1/40* (2006.01)

(52) U.S. Cl.
CPC ............ *G01N 1/34* (2013.01); *G01N 1/4077* (2013.01); *G01N 21/643* (2013.01); *G01N 21/6452* (2013.01); *B01L 2200/16* (2013.01); *B01L 2300/041* (2013.01); *B01L 2300/069* (2013.01); *B01L 2300/0845* (2013.01); *B01L 2300/12* (2013.01); *B01L 2300/123* (2013.01); *B01L 2300/161* (2013.01); *G01N 2001/4088* (2013.01)

(58) Field of Classification Search
CPC ........... B01L 2300/12; B01L 2300/123; B01L 2300/161; C07H 1/00; C07H 3/06
See application file for complete search history.

(56) References Cited

U.S. PATENT DOCUMENTS

| | | |
|---|---|---|
| 2010/0233034 A1 | 9/2010 | Olivier |
| 2013/0171658 A1 | 7/2013 | Fulton |
| 2014/0038215 A1 | 2/2014 | Smart et al. |
| 2016/0025606 A1 | 1/2016 | Oroskar |
| 2018/0156809 A1* | 6/2018 | Kimzey ............... G01N 33/582 |

FOREIGN PATENT DOCUMENTS

| | | |
|---|---|---|
| WO | WO2012107572 A1 | 8/2012 |
| WO | WO2016/003795 A1 | 1/2016 |
| WO | WO2016100447 A1 | 6/2016 |

OTHER PUBLICATIONS

Young, Lee W., International Search Report, Intl. Appln. PCT/US2018/023875, dated Aug. 1, 2018.
Young, Lee W., Written Opinion of the International Searching Authority, Intl. Appln. PCT/US2018/023875, dated Aug. 1, 2018.
Jiang, Kuan et al., Solid-phase reductive amination for glycomic analysis, Analytica Chimica Acta, Jan. 31, 2017, pp. 32-40, v. 962.
Anonymous, Solid Phase Extraction Products Improve Sensitivity and Increase Throughput, Sigma-Aldrich, Jan. 1, 2015, XP055754609, www.sigmaaldrich.com/content/dam/sigma-aldrich/.
Svacinova, Jana et al., A new approach for cytokinin isolation from *Arabidoposis* tissues using miniaturized purification: pipette, Plant Methods, Jan. 1, 2012, p. 17, v. 8(1).
Anonymous, AdvanceBio N-Glycan Sample Preparation Kit User Guide (96 samples) p/n 5190-8005, Feb. 24, 2015, XP055756514, www.agilent.com/cs/library/usermanuals/public/AdvanceBio%.
Lopez Garcia, F., EPO Supplementary European Search Report, Appln. EP 18771481, Dec. 15, 2020.

* cited by examiner

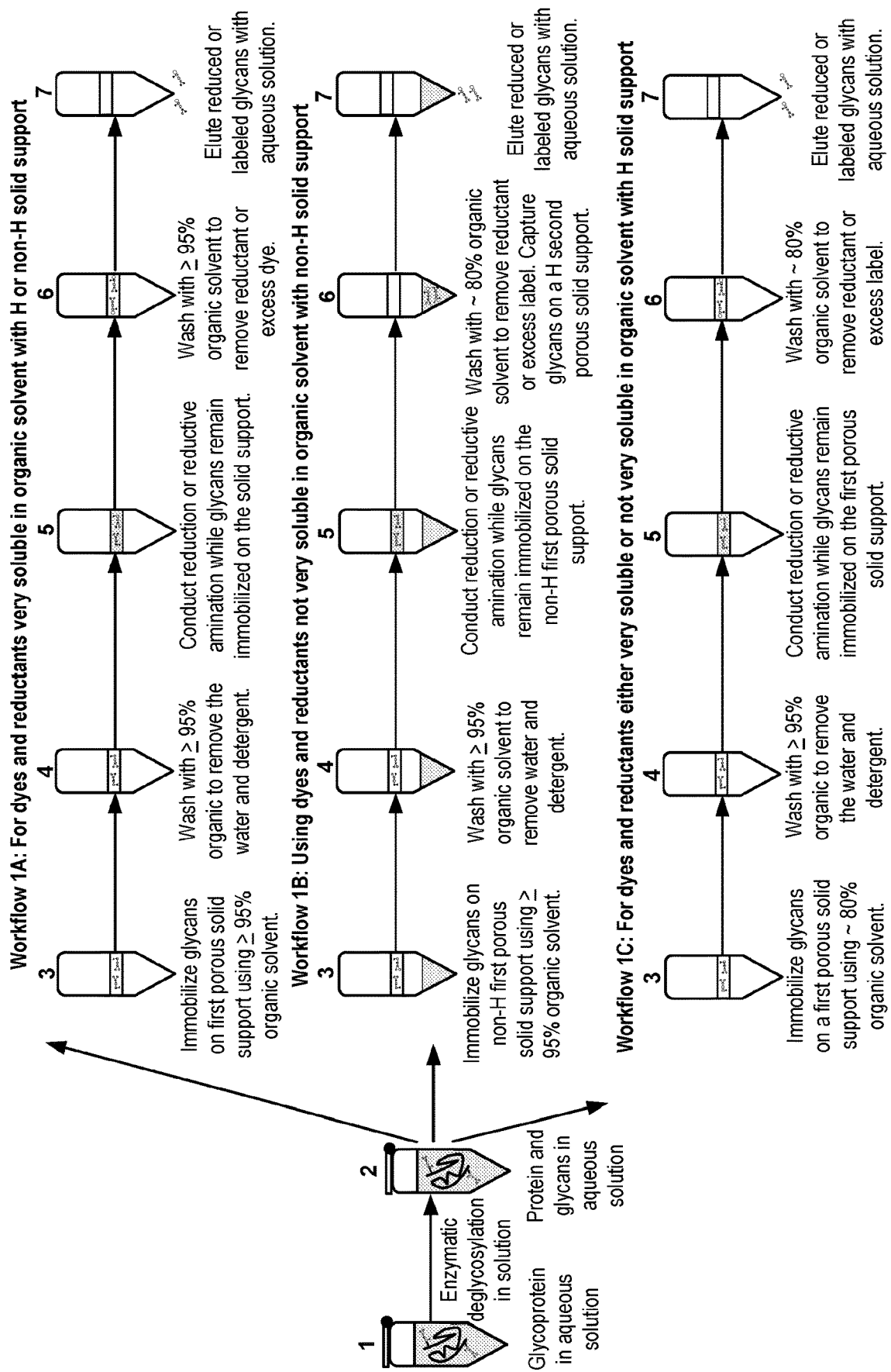

DEVICES AND KITS TO IMPROVE REDUCTION OR LABELING OF CARBOHYDRATES

CROSS-REFERENCE TO RELATED APPLICATIONS

This is a continuation of International Application No. PCT/US2018/023875, filed Mar. 22, 2018, which is hereby incorporated by reference for all purposes. This application further claims the benefit of, and priority to, U.S. Provisional Patent Application No. 62/475,815, filed Mar. 23, 2017, U.S. Provisional Patent Application No. 62/636,815, filed Feb. 28, 2018, and U.S. Provisional Patent Application No. 62/644,460, filed Mar. 17, 2018, the contents of each of which is incorporated herein by reference for all purposes.

STATEMENT OF FEDERAL FUNDING

Not applicable.

BACKGROUND OF THE INVENTION

This invention relates to the field of improving the efficiency, ease, and speed of labeling carbohydrates, such as oligosaccharides, by reductive amination.

It is necessary to determine the nature and amount of carbohydrates present in a sample in a variety of commercial and regulatory contexts. This is particularly true in the case of the glycans attached to glycoproteins, and particularly for glycoproteins used as therapeutic agents. Since the glycans attached to the glycoprotein can affect characteristics critical to the glycoprotein's function, including its pharmacokinetics, stability, bioactivity, and immunogenicity, it is important to determine which glycans are present on the glycoprotein. Characterization of carbohydrates attached to biologics (such as therapeutic glycoproteins and vaccines) is required by the Food and Drug Administration to show composition of matter and consistency of manufacture, resulting in a need for extensive characterization of the product. Analysis of the profile of the carbohydrates is also important for quality control in the production of both therapeutic and non-therapeutic recombinant proteins, in which a change in carbohydrate profile may indicate stress in the system, signaling conditions that may require the contents of a commercial-scale fermenter to be discarded. There is therefore considerable interest by biochemists, clinical chemists, pharmaceutical manufacturers, and protein producers in determining the distribution profiles of glycans in biological samples, such as therapeutic glycoproteins.

One common method of analyzing carbohydrates, and particularly of analyzing glycans released from a glycoprotein by enzymatic digestion, is labeling with an appropriate dye or label using reductive amination. For example, reductive amination of N-glycans released from a glycoprotein by the common deglycosylation enzyme PNGase F is typically accomplished by conjugating the free-reducing ends of the glycans to the free amino groups of a label, such as a fluorescent dye or a moiety with an electrical charge. One common label used for reductive amination is 2-aminobenzamide, or "2-AB." Reductive amination and labeling with 2-AB is disclosed in co-owned U.S. Pat. No. 5,747,347. Depending on the label used, the labeled glycans can then be analyzed by any of a variety of analytical methods, such as high performance liquid chromatography ("HPLC"), capillary electrophoresis ("CE", including capillary zone electrophoresis, capillary gel electrophoresis, capillary isoelectric focusing, capillary isotachophoresis, and micellar electrokinetic chromatography), or microfluidic separation. Labeling and analysis of N-glycans is further taught in, for example, co-owned U.S. Pat. Nos. 8,124,792 and 8,445,292. International Publication No. WO 2015/166399 discloses the use of magnetic beads derivatized with carboxyl groups in deglycosylation and labeling procedures.

There remains a need in the art for methods that improve the speed and efficiency of labeling of carbohydrates, such as glycans, and, in particular, the speed and efficiency of labeling of carbohydrates, such as glycans, by reductive amination. Surprisingly, the present invention meets these and other needs.

BRIEF SUMMARY OF THE INVENTION

The invention provides methods, devices, and kits for improved reduction or labeling by reductive amination of carbohydrates.

In some embodiments, the invention provides in vitro methods for reducing or labeling by reductive amination carbohydrates provided in an aqueous solution and, optionally, for analyzing the reduced or said labeled carbohydrates, comprising the following steps in the following order: (a) mixing the carbohydrates and the aqueous solution with organic solvent to create a mixture of the organic solvent and the carbohydrates in the aqueous solution having a concentration of about 80% organic solvent or more to about 20% or less aqueous solution, (b) transferring the carbohydrates in the mixture to a reaction container having (1) a first opening allowing introduction of reagents, (2) a body having, in the following order, a first section having a cross section having an area, a first porous solid support disposed across the area of the cross section of said first section, a second section having a cross section having an area, and a second opening, to allow exit of reagents when such exit is desired, (c) passing the mixture through the first porous solid support, under conditions allowing retention of the carbohydrates on the first porous solid support, thereby immobilizing the carbohydrates on the first porous solid support, (d) washing the carbohydrates immobilized on the first porous solid support with organic solvent or a solution with a concentration of organic solvent higher than 95% to remove the mixture of the organic solvent and aqueous solution and any compounds in the mixture that have not been retained on the first porous solid support, and (e) reducing or labeling by reductive amination the immobilized carbohydrates on the first porous solid support, thereby reducing or labeling by reductive amination said carbohydrates. In some embodiments, the method further comprises step e', washing any excess reductant or label from the first porous solid support using organic solvent or a solution with a concentration of organic solvent higher than 95% organic solvent following the reduction or labeling. In some embodiments, the method further comprises step e", eluting the washed reduced or labeled carbohydrates from the first porous solid support using an aqueous solution comprising up to 20% organic solvent following the wash. In some embodiments, the aqueous solution comprising up to 20% organic solvent comprises water or a buffer solution. In some embodiments, the aqueous solution does not comprise any organic solvent. In some embodiments, the first porous solid support is made of a hydrophilic material or has a hydrophilic material, other than one bearing carboxyl groups, on its surface. In some embodiments, the first porous solid support is made of a hydrophilic material. In some embodiments, the hydrophilic material is cellulose, glass, alumina, functionalized surfaces containing diol, aminopropyl, amide, cyanopropyl, ethylenediamine-N-propyl, silica, silica derivatized with diol, aminopropyl, or amide (carbamoyl), a porous hydrophilic material other than one bearing one or more carboxyl groups, or a combination of two or more of these. In some embodiments, the glass is glass fiber. In some embodiments, the first porous solid support is made of a non-hydrophilic material or has a surface of non-hydrophilic material and said mixture of said organic solvent and said carbohydrates in said aqueous solution in step (a) has a concentration of organic solvent that is over 95%. In some embodiments, the first porous solid support is made of a non-hydrophilic material. In some embodiments, the non-hydrophilic material has pores or openings of 10 microns in width or smaller. In some embodiments, the pores or openings are 5 microns in width or smaller. In some embodiments, the pores or openings are 1 micron in width or smaller. In some embodiments, the non-hydrophilic material is polyethylene, nylon, polyvinylidene fluoride, or polypropylene. In some embodiments, non-hydrophilic material has pores or openings of 10 microns or smaller. In some embodiments, the non-hydrophilic material is polyethylene. In some embodiments, (1) the reaction container of step (b) further comprises a hydrophilic second porous solid support disposed between the first porous solid support and the second opening and (2) the reducing or the labeling in step (e) is by a reductant or a label that is not very soluble in organic solvent. In some embodiments, the methods further comprise washing the reductant or label that is not very soluble in organic solvent with a wash solution comprising about 80% to 90% organic solvent and the remainder aqueous solution, thereby releasing the reduced or the labeled carbohydrates from the first porous solid support and capturing them on the hydrophilic second porous solid support. In some embodiments, the concentration of said organic solvent in said wash solution is about 80%. In some embodiments, the methods further comprise eluting the captured released labeled carbohydrates from the hydrophilic second porous solid support with an aqueous solution comprising not more than 20% organic solvent. In some embodiments, the aqueous solution comprising up to 20% organic solvent comprises water or a buffer solution. In some embodiments, the aqueous solution does not comprise any organic solvent. In some embodiments, the hydrophilic second porous solid support is made of (a) cellulose, (b) glass, (c) alumina, (d) silica, (e) functionalized surfaces containing diol, aminopropyl, amide (carbamoyl), cyanopropyl, ethylenediamine-N-propyl, or Zwitterionic groups, (f) silica covalently bonded to one or more carbamoyl groups, or (g) a combination of two or more of these. In some embodiments, the second porous solid support is made of silica. In some embodiments, the silica is covalently bonded to one or more carbamoyl groups. In some embodiments, the silica is in the form of beads or particles. In some embodiments, the silica beads or particles are from 3-60 microns in size. In some embodiments, the silica spheres or particles are about 30 microns in size. In some embodiments, the silica beads or particles covalently bonded to carbamoyl groups are Amide-80. In some embodiments, the first porous solid support is in the form of a membrane. In some embodiments, the first porous solid support is in the form of a monolith. In some embodiments, in step (e), the carbohydrates are reduced by a reductant. In some of these embodiments, the reductant is sodium cyanoborohydride or picoline borane. In some embodiments, the reductant is in an organic solvent. In some embodiments, in step (e), the carbohydrates are labeled with a label. In some of these embodiments, the label is 2-aminobenzamide (2-AB), anthranilic acid (2-AA), 8-aminopyrene-1,3,6-trisulfonic acid (APTS), or procainamide hydrochloride. In some embodiments, the methods further comprise step (f), eluting the reduced or labeled carbohydrates from the first porous solid support and separating them, analyzing them, or both. In some embodiments, the reduced or labeled carbohydrates are provided to a separation means. In some embodiments, the separation means is a device for subjecting the reduced or labeled carbohydrates to high-performance liquid chromatography, capillary electrophoresis, microfluidic separation, hydrophilic interaction liquid chromatography, or mass spectrometry, or a combination of two or more of these, thereby separating the reduced or labeled carbohydrates. In some embodiments, the reduced or labeled carbohydrates are reduced carbohydrates and the reduced carbohydrates are analyzed by mass spectrometry. In some embodiments, the reduced or labeled carbohydrates are labeled carbohydrates and the separated labeled carbohydrates are analyzed by detecting fluorescence of the labels. In some embodiments, the organic solvent is acetonitrile, absolute ethanol, absolute methanol, isopropanol, butanol, toluene, ethyl acetate, acetone, tetrahydrofuran, diethyl ether, dichloromethane, chloroform, tert-buthyl-methyl ether, benzene, carbon tetrachloride, isooctane, hexane, or a combination of any two or more of these. In some embodiments, the organic solvent is acetonitrile. In some embodiments, the carbohydrates are N-glycans. In some embodiments, the carbohydrates are O-glycans. In some embodiments, the carbohydrates are polysaccharides, oligosaccharides, disaccharides or monosaccharides. In some embodiments, the reaction container is a well. In some embodiments, the reaction container is a lumen of a microfluidic device. In some embodiments, the well is in a multi-well plate and the first porous solid support is composed of polyethylene. In some embodiments, the polyethylene has pores of 10 microns or less. In some embodiments, the container further comprises a hydrophilic second porous solid support disposed between the first porous solid support and the second opening. In some embodiments, the hydrophilic second porous solid support is composed of silica beads or particles bonded to carbamoyl groups.

In another group of embodiments, the invention provides devices for reducing or labeling by reductive amination carbohydrates provided in an aqueous solution. The inventive devices comprise a reaction container having a body with (a) a first opening, (b) a first section with a first lumen having a first cross section having an area, which first lumen is fluidly connected to the first opening, (c) a second section having a second lumen with a second cross section having an area, which second lumen is fluidly connected to the first lumen of the first section, (d) a second opening fluidly connected to the second lumen, (e) a first porous solid support disposed between the first opening and the second opening and filling the area of the first cross section of the first lumen, and (f) a second porous solid support composed of a hydrophilic material or having a surface of hydrophilic material, which second porous solid support is disposed between the first porous solid support and the second opening and fills the area of the first cross section or of the second cross section. In some embodiments, the diameter of the first section of the body of the container is wider than the second diameter of the second section. In some embodiments, the first porous solid support is disposed in the first section of the reaction container and the second porous solid support is disposed in the second section of said reaction container. In some embodiments, the reaction container is a tube or cartridge. In some embodiments, the reaction container is a well in a multiwell plate. In some of these embodiments, the second section of the well is a nozzle protruding from the bottom of the well. In some embodiments, the second porous solid support is disposed in the nozzle. In some embodiments, the reaction container is within a microfluidic apparatus. In some embodiments, the first porous solid support is made of a non-hydrophilic material or has a surface of a non-hydrophilic material. In some embodiments, the non-hydrophilic material of the first porous solid support has pores or openings of 10 microns or less in width. In some embodiments, the non-hydrophilic material is polyethylene and has pores or openings of 10 microns or less in width. In some embodiments, the first porous solid support is composed of a hydrophilic material. In some embodiments, the hydrophilic material is made of (a) glass fibers, (b) cellulose, (c) silica beads or particles, or (d) silica beads or particles covalently linked to a plurality of aminopropyl, diol, carbamoyl groups, Zwitterionic groups, or a mixture of two or more of said groups. In some embodiments, the first porous solid support is composed of glass fibers. In some embodiments, the hydrophilic material of the second porous solid support is made of (a) glass fibers, (b) cellulose, (c) silica, (d) a surface covalently linked to a plurality of aminopropyl, diol, carbamoyl groups, Zwitterionic groups, or a mixture of two or more of said groups, or (e) silica covalently linked to a plurality of aminopropyl, diol, or carbamoyl groups, or a mixture of two or more of said groups. In some embodiments, the hydrophilic material of the second porous solid support is composed of glass fibers. In some embodiments, the silica is in the form of beads or particles. In some embodiments, the beads or particles are covalently linked to a plurality of carbamoyl groups. In some embodiments, the silica beads or particles having a plurality of carbamoyl groups are Amide-80. In some embodiments, the first porous solid support is polyethylene having pores or openings 10 microns or less in width and the second porous solid support is composed of silica beads or particles covalently linked to a plurality of carbamoyl groups. In some embodiments, the silica beads or particles having a plurality of carbamoyl groups are Amide-80. In some embodiments, the second opening has an openable cover to retain solutions in the reaction container until their exit is desired.

In yet a further group of embodiments, the invention provides kits for reducing carbohydrates or labeling carbohydrates by reductive amination. The kits comprise: (a) a reaction container having a body with (a) a first opening, (b) a first section with a first lumen having a first cross section having an area, which first lumen is fluidly connected to the first opening, (c) a second section having a second diameter and a second cross section having an area, with a second lumen with a cross section having an area, which second lumen is fluidly connected to the first lumen of the first section, (d) a second opening fluidly connected to the second lumen, (e) a first porous solid support disposed between the first opening and the second opening and filling the area of the first cross section of the first lumen, and (f) a second porous solid support composed of a hydrophilic material, which second porous solid support is disposed between the first porous solid support and the second opening and fills the area of said first cross section or of the second cross section, (b) a reductant, or a label suitable for labeling carbohydrates by reductive amination, or both, and, (c) instructions for reducing carbohydrates or for labeling carbohydrates by reductive amination, or both. In some embodiments, the reaction container is a well in a multiwell plate, a tube, or a cartridge. In some embodiments, the reaction container is a well in a multiwell plate. In some embodiments, the second section of said well is a nozzle protruding from a bottom of the well. In some embodiments, the first porous solid support is polyethylene having pores or openings 10 microns or less in width and the second porous solid support is composed of silica beads or particles covalently linked to a plurality of carbamoyl groups. In some embodiments, the silica beads or particles covalently linked to a plurality of carbamoyl groups are disposed in the nozzle protruding from the bottom of the well. In some embodiments, the label is 2-aminobenzamide (2-AB), anthranilic acid (2-AA), 8-aminopyrene-1,3,6-trisulfonic acid (APTS), or procainamide hydrochloride. In some embodiments, the reductant is sodium cyanoborohydride or picoline borane, or both. In some embodiments, the kits further comprise one or more reagents for deglycosylating glycoconjugates. In some embodiments, the one or more reagents is a deglycosylation enzyme. In some embodiments, the deglycosylation enzyme is PNGase F.

BRIEF DESCRIPTION OF THE DRAWINGS

FIG. 1 is a diagram showing exemplar embodiments of the inventive methods, using glycans as exemplar carbohydrates to be reduced or labeled. Step 1 on the left depicts a container holding a glycoprotein in an aqueous solution. Legend: folded, solid line: protein component of the glycoprotein molecule. Light and dark geometric shapes: glycans attached to the glycoprotein. Thin straight line between the shapes representing the glycans and the thicker line representing the protein component: the covalent attachment of the glycans to the protein. An arrow between step 1 and step 2 represents the addition of a deglycosylation enzyme to the aqueous solution and subsequent enzymatic digestion of the glycoprotein, thereby creating a starting aqueous solution sample. To the right of step 2 are arrows pointing towards depictions of Workflows 1A, 1B and 1C. The three workflows exemplify how to adjust the workflow for the practitioner's choice of a hydrophilic ("H") or non-hydrophilic ("non-H") material for the first porous solid support and for the solubility in organic solvent of the reductant or dye to be used for reducing, or for labeling, the glycans. Workflow 1A shows embodiments in which the dye or reductant is very soluble in organic solvent, and can be used whether the first porous solid support is hydrophilic or non-hydrophilic. Workflow 1B shows embodiments in which the dye or reductant is not very soluble in organic solvent, and the first porous solid support is non-hydrophilic. Workflow 1C depicts embodiments in which the dye or reductant is or is not very soluble in organic solvent, and the first porous solid support is hydrophilic. The arrows between steps 2 and 3 represent the addition of enough organic solvent to the starting aqueous solution with the glycans released from the glycoprotein to create a mixture with the concentration of organic solvent stated in step 3 of the respective workflow. Step 3 of each workflow shows the concentration of organic solvent in the solutions used to immobilize the glycans on the first porous solid support and, in steps 4 and 6, the concentrations of organic solvent in the washes used to wash unwanted components in the solution from the first porous solid support. In step 7 of each workflow, the glycans are eluted by an aqueous solution for separation, analysis, or both. Not shown: openings at the top of the containers, allowing introduction of reagents, and openings at the bottom of the containers, allowing reagents to exit when desired.

DETAILED DESCRIPTION

Introduction

As set forth in the Background, analysis of carbohydrates, and particularly of glycans attached to glycoproteins, has become important for various regulatory and quality control purposes. In particular, analyzing the types of glycans attached to therapeutic glycoproteins such as monoclonal antibodies, and the amount of each type of glycan, has become an important quality control measurement in the production of such glycoproteins and in confirming that they will have the desired pharmacological activity.

Carbohydrates are typically analyzed by labeling them and then analyzing the labeled carbohydrates using suitable instrumentation. For example, glycans released from a glycoprotein by enzymatic digestion can be labeled by subjecting the glycans to reductive amination with an appropriate dye, as disclosed in co-owned U.S. Pat. No. 5,747,347 (hereinafter, "the '347 patent"), the contents are which are hereby incorporated by reference, and then analyzing them by detecting fluorescence of the dye attached to the labeled glycans. Release of glycans by enzymatic digestion, however, usually occurs in an aqueous solution and the glycans released from the glycoprotein are usually in an aqueous solvent. Further, carbohydrates from other biomolecules and other biological sources are usually present in aqueous environments. Labeling carbohydrates by reductive amination, however, usually requires anhydrous conditions. Thus, carbohydrates, such as the glycans released from glycoproteins, have to be dried to provide the anhydrous conditions that allow reductive amination to occur. This drying step introduces what is often considerable delay into labeling protocols for carbohydrates, and also often introduces handling and variability concerns as well.

Further, protocols for reductive amination typically require that the carbohydrate be separated from other types of molecules that may be present in a sample mixture. For example, free carbohydrates in nature are typically in complex aqueous biomatrices that may contain salts, proteins, lipids and other small metabolites, while protocols to release glycans from glycoproteins or other glycoconjugates typically result in the released glycans being in solution with other reagents, such as buffer salts, denaturing reagents, and reductants. The glycans or other carbohydrates of interest in the mixture are therefore normally subjected to a clean-up step, for example, by solid phase extraction, filtration, or gel separation, after which the glycans or other carbohydrate of interest are eluted in a suitable solvent, followed by solvent removal by evaporation. These clean-up steps, however, typically increase the amount of solvent present which then has to be dried down, and add to the time required for the overall protocol. Once dried, the purified glycans or other carbohydrates of interest are then typically reconstituted or redissolved in a suitable non-aqueous solvent and labeled by reductive amination. After the reaction is finished, further purification is usually performed to remove any excess of reactants, and in particular, any excess of free dye. This second purification is typically performed by solid phase extraction, using a stationary phase that may or may not be the same as that used to purify the unlabeled glycans or carbohydrate.

Surprisingly, the inventive methods reduce both the time and steps needed to label carbohydrates by reductive amination and to prepare them for analysis, while also reducing potential sample loss. More specifically, the inventive methods surprisingly eliminate the need for a separate step and transfers of the carbohydrates of interest first to and then from a solid phase extraction ("SPE") cartridge, and eliminate the need for a separate dry down step to remove the carbohydrates from the aqueous solution in which they are typically initially present, and thereby prepare them for reductive amination. The combination of features afforded by the inventive methods therefore provides a significant advance in the speed, efficiency, and ease in performing analysis of carbohydrates of interest. The combination of features is especially useful in labeling glycans released from glycoproteins by enzymatic digestion. In another aspect, the invention provides devices for labeling carbohydrates with the label APTS (8-aminopyrene-1,3,6-trisulfonic acid, CAS No. 196504-57-1), or other reductive amination dyes that are not very soluble in organic solvents. Similarly, the inventive devices exploit the inventive methods to allow workflows that both increase the speed of the labeling, and reduce the number of transfers between containers that could lead to loss of sample.

Surprisingly, in some embodiments, the inventive methods can further be used to reduce glycans or other carbohydrates while they are immobilized on a solid support without labeling the glycans or other carbohydrates. As persons of skill are aware, glycans and other carbohydrates occur in two anomers, designated alpha and beta. Each anomer of an unreduced carbohydrate results in a separate signal when that carbohydrate is present in a sample under analysis (for example, there will be two peaks for each unreduced carbohydrate analyzed by mass spectrometry), while reduced carbohydrates have only one anomeric form and result in only one signal or peak for each carbohydrate. Thus, in embodiments in which carbohydrates are reduced while immobilized on the first porous solid support, but not labeled, the sensitivity of detecting the presence of the carbohydrates in the sample is improved and the analysis of the carbohydrates present is simplified.

This section starts first with an overview of aspects of the inventive methods, which is the followed by more specific descriptions of particular aspects and variations that can be made to address, for example, different starting solutions, different reductants or dyes for labeling the carbohydrates, and different types of containers. Further, the section provides a description of the inventive devices for workflows using reductants or labeling dyes, such as APTS, that are not very soluble in organic solvents.

The starting point for the inventive methods is a sample containing one or more carbohydrates which the practitioner wishes to label by reductive amination for later analysis, for example by measuring fluorescence of the resulting labeled carbohydrates, or which the practitioner wishes to reduce without labeling and to then analyze by mass spectrometry. The glycans or other carbohydrates are typically present in an aqueous solution, although in some instances, they may be in a dried sample that is then resolubilized in an aqueous solution. For example, the aqueous solution may be the solution resulting from an enzymatic digestion of a glycoprotein with a deglycosylation enzyme, and comprise (i) the aqueous buffer in which the enzymatic digestion was performed, (ii) the fully or partially aglycosylated protein remaining after glycans have been released by action of the enzyme, (iii) any glycans released by the enzymatic digestion, (iv) the deglycosylation enzyme, (v) buffer salts, (vi) reductants, and (vii) other denaturants. In other embodiments, the carbohydrates may be in a biological or other sample which also contains lipids, proteins, salts, and other metabolites. For convenience of reference, the aqueous solution containing the carbohydrate(s) to be labeled, along with any other reagents present in the solution, will sometimes be referred to herein as the "starting aqueous solution sample." Depending on the equipment used, the starting aqueous solution sample is typically contained in a container, such as a well, an Eppendorf tube, or the lumen of a microfluidic device. The container in which the starting aqueous solution sample is provided will sometimes be referred to below as the "initial container."

In typical current protocols, a purification step is used to separate the carbohydrates from any proteins, lipids, or other non-carbohydrate molecules that are present in the sample, resulting in isolated carbohydrates that can then be subjected to labeling by reductive amination. Typically, this purification step is done by transferring the sample into a solid phase extraction ("SPE") cartridge, eluting the non-carbohydrate components from the cartridge, and then eluting the now-isolated carbohydrates to a separate well or vial for reductive amination, or by using a material that retain the non-carbohydrate components, but not the carbohydrates, allowing the carbohydrates to flow through and be collected.

Surprisingly, the inventive methods eliminate the need in the workflow for a separate purification step and multiple transfers of the sample and carbohydrate, thereby reducing both the time for the procedure and the chance for loss of sample from multiple transfers of sample from one container to another. Further, the materials used in many embodiments are inexpensive, and are readily automated. Thus, the inventive methods provide a combination of advantages not previously available in the art.

The inventive methods exploit the properties, such as reduced solubility, of glycans or other carbohydrates when in organic solvents, as compared to their solubility in aqueous solutions. This permits immobilizing the glycans or other carbohydrates in the sample on a first porous solid support, while at the same time both washing away molecules in the sample that are soluble in the organic solvent and providing anhydrous conditions. The glycans or other carbohydrates in the sample can then be reduced or labeled by reductive amination under anhydrous conditions while they remain immobilized on the first porous solid support, following which they can then be eluted from the first porous solid support by redissolving them in an aqueous solution (usually after first washing away any reductant or, in the case of reductive amination, any label that has not bound to the glycans or other carbohydrates). The reduced or labeled glycans or other carbohydrates can then be separated and analyzed by providing them to separation means, analytical means or, preferably, first to a separation means and then to an analytical means.

In some of these inventive methods, the first porous solid support is of a hydrophilic material and organic solvent is added to the starting aqueous solution containing the glycans or other carbohydrates of interest to create a mixture that has a concentration of organic solvent that is 75-95% organic solvent, as shown in FIG. 1 in Workflow 1A, or a mixture that has a concentration of organic solvent above 95%, as shown in Workflow 1C. Without wishing to be bound by theory, it is believed that at concentrations of organic solvent from 75% to 95%, the glycans or other carbohydrates present in the sample are retained on the hydrophilic first porous solid support by hydrophilic interactions, while at concentrations of organic solvent over 95%, it is believed that the glycans or other carbohydrates in the sample precipitate or aggregate, and can be captured and retained on the first porous solid support by simple filtration through pores or openings in first porous solid support regardless of whether the first porous solid support is hydrophilic or non-hydrophilic. Thus, adding organic solvent to the starting aqueous solution sample to create a mixture with a concentration of organic solvent above 95% permits the use of a broader range of materials for the first porous solid support than does the use of organic solvent to create a mixture with a concentration of organic solvent at or below 95%.

In the inventive methods, the starting aqueous solution sample containing the glycans or other carbohydrates of interest (and which may also contain proteins, denaturants, salts, enzymes, or other compounds) is in an initial container. The starting aqueous solution sample is then mixed with organic solvent so that it is in the chosen concentration of organic solvent (i.e., 75-95% for use with a hydrophilic first porous solid support where capture on the first porous solid support by hydrophilic interaction is desired, or greater than 95% for use with a hydrophilic or a non-hydrophilic first porous solid support where capture on the first porous solid support by simple filtration is desired) at the time the mixture with the starting aqueous solution sample comes into contact with the first porous solid support. Persons of skill will appreciate that there are a number of ways to accomplish this. For example, organic solvent in amounts to create the desired concentration of organic solvent can be added to the container initially holding the starting aqueous solution sample. Or, the starting aqueous solution sample can be transferred to a larger container and mixed with organic solvent to create a mixture having the desired concentration of organic solvent before adding it to a container with the first porous solid support. Alternatively, a quantity of organic solvent can be present in the container holding the first porous solid support so that, when the starting aqueous solution sample is added to the container, the mixture of the organic solvent and starting aqueous solution sample creates a mixture with the desired concentration of organic solvent. Finally, one can start adding the desired amount of organic solvent to the container holding the first porous solid support and start adding the starting aqueous solution sample to the container slowly enough so that the mixture of the organic solvent and starting aqueous solution sample in the container at the first porous solid support is always at or above the desired concentration of organic solvent to starting aqueous solution sample.

In studies underlying the present disclosure, organic solvent was typically added to a second container in an amount that would create a mixture with concentrations of organic solvent at or above 80%, and the organic solvent was then spiked by adding the starting aqueous solution sample. For example, in these studies, 80 microliters of organic solvent would be spiked with 20 microliters of starting aqueous solution sample. The resulting mixture was then transferred to a container holding a first porous solid support.

For convenience of reference, the container holding the first porous solid support will sometimes be referred to herein as the "reaction container." (In microfluidics apparatuses, the starting aqueous solution sample is not transferred to a separate container holding the first porous solid support, but rather from a first section of a channel, tubing, or the like to a second section of channel, tubing, or the like, which second section contains the first porous solid support. The phrase "reaction chamber" is sometimes used herein to denote the section of a microfluidics device configured for use in the inventive methods. For convenience of reference, the discussion below will be generally discussed with relation to embodiments in which the starting aqueous solution sample transferred to a reaction container, but will be understood to also relate to microfluidics applications in which the starting aqueous solution sample is transferred to a section comprising a space large enough to hold the mixture of organic solvent and starting aqueous solution sample and the first porous solid support, unless otherwise stated or required by context.) The reaction container has a first opening, usually at the top, through which solutions and reagents may be introduced, a body, typically cylindrical, and containing the first porous solid support, and a second opening, usually disposed at the bottom of the container, opposite the first opening. The second opening may be closable to prevent solutions from exiting the reaction container until desired. The body of the container has a lumen which has a cross section (circular, in the case of a cylindrical body) which has an area defined by the dimensions of the body. The first porous solid support is positioned in the reaction container filling the cross sectional area of the reaction chamber so that the mixture of organic solvent and starting aqueous solution sample containing the glycans or other carbohydrates has to go through pores or openings in the first porous solid support to reach the second opening.

As glycans and other carbohydrates are hydrophilic, they will tend to be retained on hydrophilic surfaces when they are in solutions that are 75%-95% organic solvent. In some preferred embodiments, the concentration of organic solvent is about 80%, with "about" in this context meaning ±2%. In some preferred embodiments, the concentration of organic solvent is 80%. Without wishing to be bound by theory, it is believed that the glycans or other carbohydrates are retained on hydrophilic surfaces under these conditions by non-covalent hydrophilic interactions rather than by filtration. Accordingly, the pore size of the first porous solid support is not critical in these embodiments, but should be small enough so that the glycans or other carbohydrates do not come into contact with the hydrophilic surface of the first porous solid support. For example, pores or openings in the first porous solid support should not be so large that drops of the starting aqueous solution sample can go through the pores or other openings without contacting the hydrophilic surface. Any particular size of pores or other openings can be readily tested for its suitability by assays such as those set forth below) Preferred materials for these embodiments include glass fibers, cellulose, alumina, aminopropyl, aspartamide, cyclodextrin, triazole, diethylaminoethyl, silica, or silica derivatized with a chemical groups such as diol, cyanopropyl, ethylenediamine-N-propyl, aminopropyl, amide (carbamoyl), Zwitterionic groups, or combinations of two or more of these, with glass fibers and derivatized silica being preferred and glass fibers being particularly preferred. The first porous solid support is one that is not derivatized with, or that uses, carboxyl groups to capture carbohydrates present in the starting aqueous solution sample and should not be made of a material, or have be derivatized with, a material that would react with reductants or the labels used in reductive amination. For example, the material should not be derivatized with a plurality of aldehydes. The material can be in the form of a membrane or a monolith shaped to fill the cross sectional area of the container, so that the solutions have to pass through the first porous solid support. In some embodiments, especially in the case of silica, however, the material for the solid support can be in the form of beads or particles, which can be held in place within the reaction container by, for example, a frame of plastic with cross hatching smaller than the diameter of the beads or particles, positioned under the beads or particles within the lumen of the container. In some embodiments, the first porous solid support can be made of an underlying material that is not hydrophilic, but has a surface layer of hydrophilic materials to permit retention of the glycans or other carbohydrates on the hydrophilic surface. In preferred embodiments, the material from which hydrophilic first porous solid supports is made is hydrophilic.

If the practitioner chooses to raise the concentration of organic solvent is raised above 95%, for example, to 99% or higher, diluting the aqueous component to the point that the glycans or other carbohydrates are in what is almost neat organic solvent, non-hydrophilic materials can be used for the first porous solid support in addition to the hydrophilic materials that can be used at lower concentrations. This allows the practitioner to use materials, such as polyethylene, nylon, polyvinylidene fluoride, or polypropylene, that are less expensive and easy in which to create pores or openings of a desired size (e.g., 10 microns or less) for the first porous solid support. As with the hydrophilic materials discussed above, the non-hydrophilic material chosen for use as the first porous solid support should not be one that contains or is derivatized with chemical groups, such as aldehydes, expected to react with reductants or labels for reductive amination. Without wishing to be bound by theory, it is believed that, in concentrations of organic solvent above 95%, glycans or other carbohydrates aggregate or precipitate out of the starting aqueous solution sample and can captured and retained on the first porous solid support by filtering them through pores or openings of 10 microns or less in the first porous solid support.

Use of a hydrophilic material with a pore size of 10 microns or less, and of organic solvent at more than a 95% concentration, also allows retention of monosaccharides and other small glyans or carbohydrates that do not precipitate well and have only weak hydrophilic interactions. Thus, depending on the particular glycans or carbohydrates of interest and the material used for the first porous solid support, the organic solvent will be added to the starting aqueous solution sample to create a mixture of 80% to more than 99% organic solvent, for example, by adding organic solvent to the starting aqueous solution sample at ratios of 4:1 to 49:1. Appropriate ratios of organic to starting aqueous solution sample and appropriate materials for the first porous solid support will be discussed in more detail below.

As noted, the material comprising the first solid support is porous, with pores or openings sized to cause the starting aqueous solution sample to percolate or filter through the first porous solid support and, at the concentration of organic solvent present, retains the glycans or other carbohydrates, while liquids, such as the aqueous component of the starting aqueous solution sample, and solutes that have remained dissolved in the mixture of organic solvent and starting aqueous solution, such as deglycosylation enzymes, proteins (glycosylated or aglycosylated), buffer salts, water, and reductants, are allowed to elute from the first porous solid support and exit the reaction container. In studies underlying the present invention, proteins were seen to precipitate in the solution and on the first porous solid support along with the glycans or other carbohydrates. The presence of the precipitated proteins did not interfere with reduction or labeling of the glycans or other carbohydrates.

The interaction between the first porous solid support and the carbohydrates is non-covalent, and therefore does not require the time or conditions that might be required to form covalent interactions between the carbohydrates and the first porous solid support. In studies underlying the present invention, in which a series of glycoproteins were deglycosylated and the resulting glycans labeled by reductive amination following the methods described herein, proteins, such as any aglycosylated proteins remaining following the deglycosylation reaction and any deglycosylation enzyme that might have bound to the first porous solid support, did not interfere with the labeling or subsequent separation and analysis of the carbohydrates.

The first porous solid support, with the retained glycans or other carbohydrates, is then preferably washed with organic solvent, either neat or in a mixture with a concentration of 95% or more organic solvent. This wash is typically very quick, but removes any water still present from the starting aqueous solution sample, or dilutes it below a point at which it will interfere with the ability to proceed with reduction or reductive amination of the carbohydrates. Thus, the wash with the organic solvent or mixture of 95% or more organic solvent removes the need for a separate drying step. As drying steps often require either considerable time to allow water in the starting aqueous solution sample to evaporate, or equipment to provide a vacuum to cause the water to evaporate quickly, eliminating the dry down step markedly reduces the time (in the case of simple evaporation) or cost and equipment (in the case of creating a vacuum to speed evaporation) required to prepare the carbohydrates for reductive amination. Further, since the separation of the carbohydrates from other components, and the removal of the aqueous solution do not require (a) transfer to a SPE cartridge, and (b) elution of the purified carbohydrates from the SPE cartridge into a container for drying, the time for these steps and the potential for losses of the carbohydrates during the transfers, are both eliminated.

Certain aspects of various embodiments of the inventive methods are now discussed to provide further explanation and guidance.

Reducing, or Reductive Amination of, Glycans or Other Carbohydrates on the First Porous Solid Support In some embodiments, the glycans or other carbohydrates are then reduced with a reductant or subjected to reductive amination with a suitable label, such as 2-AB (2-aminobenzamide), 2-AA (anthranilic acid), APTS (8-aminopyrene-1,3,6-trisulfonic acid, CAS No. 196504-57-1) or procainamide hydrochloride (CAS No. 614-39-1), under conditions (such as pH, temperature, and time) that allow the labeling of the carbohydrates by reduction amination to occur. Conditions for conducting reduction of glycans or other carbohydrates, and for reductive amination are, of course, well known in the art. For example, U.S. Pat. No. 5,747,347, which issued in 1998, teaches labeling carbohydrates with 2-AB by reductive amination. It is therefore expected that persons of skill are very familiar with reaction conditions appropriate for conducting reductive amination using labels such as those named above. (For clarity, it is noted that the labels used in reductive amination, such as 2-AB, 2-AA, or APTS, are sometimes referred to by practitioners as dyes. Following this usage in the art, the two terms may be used interchangeably herein.) In other embodiments, the glycans or other carbohydrates are reduced by use of a reductant.

In preferred embodiments, the reduction or reductive amination is conducted while the glycans or other carbohydrates are immobilized on the first porous solid support. As practitioners will appreciate, the reagent volumes used in analytical methods is very small. Once the glycans or other carbohydrates are retained on the first porous solid support, which may, for example, be a membrane, a monolith, or silica beads, the reductants or labeling materials are typically added in amounts as small as 10 to 20 microliters. Without wishing to be bound by theory, it is contemplated that reagents in such small amounts will be retained on the first porous solid support by capillary action or by surface tension. In typical embodiments, the container can then be open at the end at which the container is designed to have liquids exit the container (typically the bottom, if the container is designed so that liquids move vertically from top to bottom, or, if the container is designed to have fluids move horizontally, for example, in some a microfluidic applications in which a microfluidic tube might be designed to have fluids introduced from one side and to exit out another, out an opening other that the one from which they are introduced). If desired, however, the container can have a manual or automated means of sealing the bottom or exit area so that the reagents are retained until in the container during steps requiring their presence, and opening the bottom or exit area to permit them to drain or to be eluted from the container when desired. For example, the bottom can have a flap, cap, or other covering that, when closed over the opening, allows fluids to be retained in the container and which, when open, allows fluids to exit the container. In microfluidic applications, in which the reductive amination takes place in a reaction chamber which may be vertically disposed or horizontally disposed, there may be, for example, one or more valves between the reaction chamber and the channel or other path through which the practitioner wishes the reactants to proceed, with a valve separating the reaction chamber from a particular channel being opened to permit solutions and solvents to be eluted from the reaction chamber along the desired path. In the event the practitioner wishes to reduce glycans or other carbohydrates, or to label them by reductive amination in the larger volumes used on a preparative scale rather than on an analytical scale, having a removable cover at the bottom of the container is preferable.

Following reduction of the glycans or other carbohydrates, they may be washed to remove excess reductant. Following reductive amination, the now-labeled glycans or other carbohydrates are washed to remove any label present that has not bound to a carbohydrate ("excess" or "free" dye or label). The solvent or solution used for this wash step depends on how soluble the reductant or label is in the organic solvent to be used to wash the glycans or other carbohydrates and whether the material of the first porous solid support is or is not hydrophilic. The dyes 2-AA and 2-AB, for example, are very soluble in organic solvents, while APTS is not. For carbohydrates reduced by a reductant or labeled by a dye that is very soluble in organic solvent, the practitioner can use either Workflow 1A or, if the practitioner has used a hydrophilic first porous solid support, Workflow 1C.

In Workflow 1A, a hydrophilic or non-hydrophilic the solid support is simply washed with organic solvent, either neat or in a solution with organic solvent at a concentration of over 95% (to correspondingly less than 5% water or aqueous solution), with higher ratios of organic solvent to water or aqueous solution being preferred. In these embodiments, the reduced or labeled glycans or other carbohydrates will be retained on the first porous solid support, while the reductant or free dye elutes from the container in the wash of organic solvent or high concentration of organic solvent to water or aqueous solution. The reduced or labeled glycans or other carbohydrates are then eluted from the reaction container or chamber into a receiving container by washing the membrane with an aqueous solution. The reduced or labeled carbohydrates can then be provided to an analytical means for analysis.

If the first porous solid support is hydrophilic, the practitioner can instead use Workflow 1C. As shown in FIG. 1, in Workflow 1C, step 6, the first porous solid support is washed with organic solvent in a mixture that has a concentration of organic solvent of 75% or above. In preferred embodiments, the concentration of organic solvent is 78% or above, and is preferably about 80% with "about" in this case meaning ±2%. As noted previously, in these concentrations of organic solvent, the glycans stay on the hydrophilic first porous solid support, allowing the reductant or excess label to be washed away.

In contrast to 2-AA and 2-AB, APTS is not very soluble in organic solvent. In embodiments in which the reductant and dye chosen by the practitioner is one that is not very soluble in organic solvent, and in which the first porous solid support chosen for the reduction or labeling by reductive amination is non-hydrophilic, the workflow is modified as shown in FIG. 1, Workflow 1B. This workflow varies from that of Workflow 1A in the following respects. First, since the reductants or dyes are not very soluble in organic solvent, a solution with a higher concentration of water to organic solvent is used to wash the reductant or excess dye off the first porous solid support than is used in Workflow 1A. Typically, the wash used for APTS or other dyes or reductants that are not very soluble in organic solvent is about 75-90% organic solvent, with about 80% being preferred and the term "about" here meaning ±2% (for convenience of reference, this wash will sometimes be referred to as the "organic solvent/aqueous wash"). Appropriate concentrations of organic solvent to aqueous buffer to remove reductants or APTS or other dyes less soluble in organic solvent can be determined for any particular reductant or dye by using as a guide concentrations of solvents used in HILIC for separating carbohydrates.

Second, the reduced or labeled glycans or other carbohydrates will not remain aggregated or precipitated in the presence of concentrations of organic solvent/aqueous wash used in these embodiments and will accordingly re-dissolve and come off the first porous solid support. And, as the first porous solid support in these embodiments is made of a non-hydrophilic material, the reduced or labeled glycans or other carbohydrates will not remain on the support by hydrophilic interactions. In these embodiments, therefore, a second porous solid support, this one made of a hydrophilic material that can retain the glycans (or, in embodiments with other carbohydrates, the other carbohydrates) released from the first porous solid support, is used to capture the reduced or labeled glycans or other carbohydrates as they are released from the first porous solid support by the organic solvent/aqueous wash. Without wishing to be bound by theory, the glycans released from the non-hydrophilic first porous solid support will be retained on the hydrophilic second porous solid support by hydrophilic interactions in the presence of the organic solvent/aqueous wash.

In preferred embodiments, the second porous solid support is positioned downstream of the first solid support, along the path in which the solvents and solutions move through the container. In preferred embodiments, the second porous solid support is in the same container (or section of microfluidic channel, tubing or the like) as the first porous solid support. Like the first solid support, the second solid support is porous, which allows the solutions and dissolved reductant or excess dye to flow though and be eluted from the container but, as noted, is composed of hydrophilic material that can retain the reduced or labeled glycans or other carbohydrates in the presence of the organic solvent/ water wash used to wash the reductant or excess label from the first porous solid support. The hydrophilic second porous solid support used in these embodiments to capture glycans or other carbohydrates coming off a non-hydrophilic first porous solid support are made of any of the hydrophilic materials described above as suitable for making hydrophilic first porous solid supports (e.g., glass, cellulose, alumina, aminopropyl, aspartamide, cyclodextrin, triazole, diethylaminoethyl, silica, or silica functionalized or derivatized with a chemical group such as a diol, cyanopropyl, ethylenediamine-N-propyl, amide (carbamoyl), one or more Zwitterionic groups, or a combination of two or more of these). In some preferred embodiments, the silica or functionalized silica is in the form of beads or particles. In some preferred embodiments, the silica is functionalized or derivatized with carbamoyl. In some embodiments, the silica derivatized with carbamoyl is Amide-80 and in some embodiments is composed of beads 30 microns in size. The hydrophilic material should not be one that contains or is derivatized with chemical groups, such as aldehydes, expected to react with reductants or labels for reductive amination.

Any particular material or functional group on a material can be readily tested to see if it is hydrophilic enough for use as a hydrophilic material from which to make a second porous solid support or a hydrophilic first porous solid support. For example, a material or a functionalized material of interest can be placed in a column, a known amount of labeled carbohydrates introduced into the column in the selected organic solvent/water wash, and the fluid coming out of the column run through an analytical instrument, such as a fluorescence detector, to measure how much of the known amount of the labeled carbohydrates have exited the column. The difference between the amount of labeled carbohydrates introduced into the column and the amount exiting is the amount retained by the material being tested. Materials that retain higher amounts of labeled carbohydrates are preferred.

Turning back to the overall description of the inventive methods, once the reductant or the excess label has been washed away, the reduced or labeled glycans or other carbohydrates are eluted from the second porous solid support by washing the second porous solid support with an aqueous solution. In the embodiments depicted in FIG. 1, this step is shown as step 7 of each workflow. Typically, up to 20% of the solution used to elute the carbohydrates can be an organic solvent, but it is at least 80% aqueous solution, with higher concentrations of aqueous solution being preferred. It should be noted that the "aqueous solution" can be water, but is preferably a buffer solution, such as HEPES (2-[4-(2-hydroxyethyl)piperazin-1-yl]ethanesulfonic acid) buffer, phosphate buffered saline, or ammonium formate buffer. The presence of the salts in the buffer solutions increases the polarity of the aqueous solution, enhancing the release of the glycans or other carbohydrates from the solid support during elution. When the "glycans or other carbohydrates" are labeled glycans, the buffers help maintain the glycans in a pH controlled solution, increasing their stability.

The eluted, reduced or labeled carbohydrates are then collected and available to be provided to analytical instruments for analysis. For example, the reduced or labeled glycans or other carbohydrates can be separated by high-performance liquid chromatography, capillary electrophoresis, microfluidic separation, or hydrophilic interaction liquid chromatography ("HILIC"). Labeled glycans or other carbohydrates may then be analyzed by detecting their fluorescence and measuring the intensity of that fluorescence, by mass spectrometry, or a combination of detecting the fluorescence intensity and mass spectrometry, while reduced glycans or other carbohydrates are typically analyzed by mass spectrometry.

As persons of skill will appreciate, it is easy to determine if any particular dye is considered very soluble in any particular organic solvent or not very soluble in that organic solvent. For example, if the reductant or dye can be dissolved in the organic solvent in a clear container at a concentration of 10 mg/ml, it is considered highly soluble for these purposes. If the label being tested cannot reach that concentration in the selected organic solvent without some of the label being visible as a precipitate or remaining undissolved, then it is not highly soluble in that solvent and Workflow 1B should be used if the first porous solid support is non-hydrophilic or presents a surface that is not hydrophilic.

Some embodiments of the embodiments of the inventive methods just discussed will be better illustrated by reference to FIG. 1, which is a diagram showing several exemplar embodiments of the inventive methods. Step 1 of FIG. 1 depicts a vial containing a glycoprotein in an aqueous solution. The protein component of the glycoprotein molecule is shown as a folded, solid line, while the glycan components are shown as light and dark geometric shapes. The covalent attachment of the glycans to the protein component is represented by a thin straight line between the shapes representing the glycans and the thicker line representing the protein component. An arrow represents the addition of a deglycosylation enzyme to the aqueous solution, and step 2 depicts the result of the enzymatic digestion of the glycoprotein, resulting in glycans released from the glycoprotein. To the right of step 2 are arrows pointing depictions of Workflows 1A-1C.

In all the workflows, the arrow between steps 2 and 3 represents the addition of organic solvent to the aqueous solution in which the enzymatic digestion was performed, creating a mixture which has a concentration of organic solvent which, as shown in the respective workflows, can be about 80% or more organic solvent if the workflow employs a first porous solid support that is hydrophilic or has a surface of a hydrophilic material, or has a concentration greater than 95% organic solvent if the workflow employs a first porous solid support that is not hydrophilic. In step 3 of each workflow, the mixture with the desired concentration of organic solvent to the starting aqueous solution sample is then introduced into the reaction container, which contains the first porous solid support. In each of these exemplar workflows, the first porous solid support is shown as a membrane. In step 3, the first porous solid support (in this case, the membrane) captures and retains the glycans, represented, as before, by light and dark geometric shapes. In this FIGURE, the reaction container in the Workflows is depicted as having a cylindrical body and an inverted conical bottom, with the solution being introduced from the top of the container and passing through the membrane, which is disposed just below the middle of the cylindrical body. In Workflow 1B, the reaction container further has a second porous solid support of hydrophilic material disposed in the conical section, depicted as a shaded area within the conical portion of the container. In all three workflows, the glycans are retained on the membrane while the mixture of the starting aqueous solution and organic solvent passes through the membrane. In step 4 of each workflow, the membrane is washed with either an organic solvent or a solution that is more than 95% organic solvent to remove salts, detergents, and other unwanted components that may be present on the membrane, while the glycans remain on the first porous solid support. In step 5, reagents for reducing the glycan without labeling it, or for labeling it by reductive amination (including a label selected by the practitioner and, typically, a reductant), are introduced to the container, and reduction or reductive amination takes place while the glycans are immobilized on the membrane. In the embodiments shown in FIG. 1, the tip of the inverted conical section has an opening (not shown) allowing wash solutions and eluted reagents to exit the container. In other embodiments, the bottom of the container may have an opening that is releasably covered by a flap, cap, or other covering, which the practitioner removes manually or by an automated means when desired to permit the exit of solutions or reagents from the container. In Workflow 1A, step 6, the membrane is washed with either an organic solvent or a solution that is more than 95% organic solvent to less than 5% aqueous solution to remove the reductant or any label that has not bound to a carbohydrate. In Workflow 1B, step 6, the membrane is washed with a solution that has a lower percentage of organic solvent to aqueous solution than is used in Workflow 1A, as this workflow is used when the reductant or dye is not very soluble in organic solvent and the first porous solid support is not hydrophilic. The wash solution in the example shown in Workflow 1B is about 80% organic solvent to about 20% aqueous solution (e.g., water or a water-based buffer). The glycans will not remain on the non-hydrophilic solid support in the presence of this high a water content in the wash solution and will flow down, along with the excess dye, into the hydrophilic second porous solid support. The glycans are then captured and retained on the hydrophilic second porous solid support, while the reductant or excess dye flows out an opening at the tip of the inverted conical section. In step 7 of all the workflows, an aqueous solution is used to elute the glycans from the porous solid support on which they have been retained (in Workflows 1A and 1C, the first porous solid support and in Workflow 1B, the second porous solid support). The reduced or labeled glycans are typically eluted into a well, vial or other collection container.

It should be noted that the container shown in Workflow 1B, with two porous solid supports, can of course also be used in the workflow shown in Workflow 1A. The use of a mixture of more than 95% organic solvent to aqueous solution starting sample in step 3 and a wash solution of over 95% organic solvent in step 6 of FIG. 1A keeps the glycans on the first porous solid support, and the second porous solid support will simply be superfluous, regardless of the material from which the first porous solid support is made. Thus, a container with both supports has the flexibility to be used for either workflow.

In some preferred embodiments, the eluted reduced or labeled glycans or other carbohydrates are then separated by, for example, high-performance liquid chromatography, capillary electrophoresis, microfluidic separation, or hydrophilic interaction liquid chromatography, and are then analyzed by providing them to a selected analytical instrument. Typically, the analysis is by providing the glycans or other carbohydrates to a fluorescence detector, to a mass spectrometer, or to both.

Reducing the Glycans or Other Carbohydrates without Labeling them

As noted above, carbohydrates occur in two anomers, which can results in two signals for each carbohydrate upon analysis. Reducing the reducing end of the carbohydrates results in one anomer for each carbohydrate present in the sample, making it easier to analyze the signals and increasing sensitivity of detection. Thus, in some embodiments, the practitioner may choose to reduce the glycans or other carbohydrates immobilized on the first porous solid support without labeling them.

In these instances, the glycans or other carbohydrates are immobilized on the first porous solid support following the steps set forth above with respect to preparing the glycans or other carbohydrates for reductive amination. The immobilized glycans or other carbohydrates are then contacted with one or more reductants, typically in an organic solvent, but not a dye (such as 2-AA or 2-AB) that would be used if the glycans or other carbohydrates were being labeled by reductive amination. Suitable reductants and procedures are discussed in a separate section below.

Once the glycans or other carbohydrates are reduced, they can be eluted from the first porous solid support as described above for glycans or other carbohydrates labeled with a dye that is highly soluble in organic solvent. In some preferred embodiments, the labeled glycans or other carbohydrates are then separated by, for example, high-performance liquid chromatography, capillary electrophoresis, microfluidic separation, or hydrophilic interaction liquid chromatography, and then analyzed by providing them to a selected analytical instrument. Typically, the analysis of reduced, but not labeled, glycans or other carbohydrates is by providing them to a mass spectrometer.

Carbohydrates

The inventive methods can generally be used with respect to any carbohydrate that has a reducing end. In some preferred embodiments, the carbohydrates are polysaccharides, in some oligosaccharides, while in others, they may be disaccharides or monosaccharides. Non-starch polysaccharides, such as cellulose and hemicellulose, and pectins, and cross-linked polysaccharides (such as SEPHAROSE®), are less preferred. In some preferred embodiments, the carbohydrates to be subjected to reductive amination and labeling are glycans released from glycoconjugates by enzymatic digestion. In some preferred embodiments, the glycans are O-glycans. In some preferred embodiments, the glycans are N-glycans. In some preferred embodiments, the O-glycans or N-glycans have been released from a glycoconjugate by enzymatic digestion, as discussed below.

Glycoproteins and Enzymatic Digestion to Release Glycans

Glycoproteins are produced by eukaryotic cells after translation of the protein by the addition of covalently-linked, linear or branched chains of carbohydrates. These protein-carbohydrate conjugates are referred to as glycoproteins; the point at which the carbohydrate is attached is referred to as a glycosylation site. Polysaccharides or oligosaccharides attached to a protein are referred to as glycans. A wide range of glycans are found on the different glycosylation sites of particular glycoproteins. The particular pattern of glycans on a particular glycoprotein is determined by the specific cell line that produced the protein and the conditions under which the cells were grown.

Glycans are typically attached to glycoproteins in one of two ways. In the first, referred to as N-glycans, the glycans are attached through an N-glycosidic bond at an asparagine residue. In the second, referred to as O-glycans, glycans are attached to an oxygen atom on an amino acid residue. For example, N-acetyl-galactosamine can be enzymatically attached to an oxygen on a serine or a threonine residue.

N-glycans can be enzymatically released from glycoproteins by enzymatic cleavage by various enzymes, such as PNGase F (Peptide-N4-(acetyl-β-glucosaminyl)-asparagine amidase, EC 3.5.1.52). Removal of glycans from a glycocojugate by enzymatic activity is often referred to as "enzymatic digestion." Enzymatic digestion of N-glycans, such as by PNGase F, typically occurs in an aqueous solution, and results in the initial release of the N-glycans as β-glycosylamines, in which the free-reducing end of the released glycan is conjugated with ammonia (see, e.g., Tarentino, et al. TIGG 1993, 23, 163-170; Rasmussen J. R. J. Am. Chem. Soc. 1992, 114, 1124-1126; Risley, et al. J. Biol. Chem. 1985, 260, 15488-15494, 1985). As noted in the Background section, PNGase F-released N-glycans are often labeled by reductive amination, in which the free-reducing end of a glycan is conjugated to the free amino group of a label, such as a fluorescent dye or a moiety bearing an electrical charge. Depending on the label used, the labeled glycans can then be analyzed by any of a variety of analytical methods, such as high performance liquid chromatography ("HPLC"), capillary electrophoresis ("CE"), carbohydrate gel electrophoresis, or microfluidic separation.

Organic Solvents

Organic solvents are used in embodiments of the inventive methods to reduce the concentration of the starting aqueous solution sample to a point at or below which carbohydrates in the sample aggregate or precipitate, or both, on the first porous solid support, allowing other compounds in the sample to be removed by, for example, washing the first porous solid support with the organic solvent. In some studies underlying the present disclosure, the organic solvent used was acetonitrile, the use of which is particularly preferred. Acetonitrile is both hydrophobic and aprotic. It is anticipated that other organic solvents can be used in embodiments of the inventive methods, and organic solvents that are both hydrophobic and aprotic are preferred. A variety of other organic solvents are believed suitable for use in embodiments of the present invention, including: absolute ethanol, absolute methanol, isopropanol, butanol, toluene, ethyl acetate, acetone, tetrahydrofuran, diethyl ether, dichloromethane, chloroform, tert-buthyl-methyl ether, benzene, carbon tetrachloride, isooctane, and hexane. Mixtures of two or more organic solvents, such as those mentioned, may also be used.

Dimethyl sulfoxide ("DMSO") and dimethylformamide ("DMF") are less preferred to serve as the primary organic solvent or as a major constituent of a mixture of organic solvents for use in embodiments of the inventive methods. It is believed DMSO or DMF can be mixed with one of the organic solvents mentioned in the preceding paragraph, or with a mixture of organic solvents mentioned above, in relatively modest amounts (such as 0.1% to 2%), without affecting the ability of the solid support to retain the carbohydrates in the presence of the organic solvent or mixture of organic solvents and to allow reductive amination to proceed.

Persons of skill will appreciate that no one organic solvent can be used in all situations, on all solid supports that might be suitable for use in embodiments of the inventive methods. Further, persons of skill in the art of labeling glycans released from glycoproteins are aware that it is common to have to test combinations of reagents to determine if the combination is useful in releasing, labeling, and analyzing the glycans present on many glycoproteins and that such testing is considered routine in the art. Practitioners can readily test any particular organic solvent for its suitability with respect to any particular sample containing a carbohydrate the practitioner wishes to reduce by a particular reductant, or to label by reductive amination with a particular label, and any particular solid support on which the practitioner wishes to retain the carbohydrate for reduction or labeling, by adding an excess of the organic solvent being tested to a starting aqueous solution sample containing a known amount of a selected carbohydrate, contacting the solvent/solution mixture to the solid support of choice (whether one already known to be useful in protocols for labeling carbohydrates by reductive amination or a solid support being tested for its utility for this purpose), reducing the carbohydrate or labeling it by reductive amination with 2-AB, washing the solid support with the organic solvent to remove label that has not bound the carbohydrate, eluting the carbohydrate from the solid support with an aqueous buffer, and subjecting the eluted solution to analysis to determine if the carbohydrate has been reduced or labeled and, if so, whether it is present in the amounts expected. If reduced or labeled carbohydrate, respectively, is not identified in the analyzed eluant in the amount expected, this indicates that the particular combination of organic solvent, of reductant or label, and of solid support, was not suitable for reducing or for labeling the selected carbohydrate by reductive amination with the selected reductant or label.

Contacting the Starting Aqueous Solution Sample with the Organic Solvent

A glycan or other carbohydrate to be labeled or to be reduced without labeling can be obtained in a variety of ways. In some embodiments, the carbohydrates of interest are glycans attached to a glycoprotein which are released into an aqueous solution by incubation with a deglycosylation enzyme, such as the exemplar deglycosylation enzyme PNGase F. In other embodiments, the glycans or other carbohydrates of interest are already present in an aqueous solution. In either embodiment, the aqueous solution containing the glycans or other carbohydrates of interest is present in a first container, which for convenience may sometimes be referred to herein as the "sample container." The aqueous solution is transferred from the sample container to a second container, such as a tube, a cartridge, a well of a multi-well plate, or a discrete section of a microfluidic apparatus. The second container may already have disposed within it the first porous solid support or the first porous solid support may be disposed in the second container after the aqueous solution has been transferred into the second container. For convenience of reference, the second container may sometimes be referred to herein as the "second container" or "reaction container." Amounts of the organic solvent sufficient to cause the glycans or other carbohydrates in the aqueous sample to be retained on the first porous solid support can already be present in the second container when the aqueous solution is introduced into it, or amounts of organic solvent sufficient to cause the glycans or other carbohydrates in the aqueous sample to be retained on the first porous solid support may be introduced into the second container after the aqueous solution containing the glycans or other carbohydrates is transferred into the second container.

As noted, in some embodiments, the reduction or the labeling of the glycans or other carbohydrates of interest may be performed in a microfluidic device. Some microfluidic apparatuses are already used to release glycans from glycoproteins by enzymatic digestion. Typically, the area of such apparatuses in which the enzymatic digestion takes place, which may for convenience be referred to as the "first chamber", is not designed to have sufficient space for the first solid support and for a sufficient amount of organic solvent to be introduced into the aqueous solution to cause the glycans or other carbohydrates in the aqueous sample to be retained on the first porous solid support. Conveniently, the apparatus may be designed to flow the aqueous solution containing the released glycans from the first chamber to a second, larger chamber within the microfluidic device which contains the first solid support and which also has enough room for an amount of organic solvent to be introduced sufficient to cause the glycans to aggregate, precipitate, or both, on the first solid support. Once the glycans have bound to the first solid support, organic solvent is then used to wash away any remaining aqueous solution to provide anhydrous conditions to allow reduction of the glycans or labeling of the glycans by reductive amination to be conducted in the second chamber.

In some embodiments, the carbohydrates can be present in a mixture or sample. For example, the practitioner may wish to reduce or to label by reductive amination carbohydrates present in a cell lysate or in a sonicated sample of tissue. The lysate or sonicated tissue can be placed in a well, tube, cartridge, or other container with the solid support, or the solid support can be added to the container after the lysate or sonicated tissue is placed in the container. Organic solvent can be present in the container when the lysate or sonicated tissue is added, or can be added afterwards to cause carbohydrates in the lysate or tissue to cause the glycans or other carbohydrates in the aqueous sample to be retained on the first porous solid support. The lysate or sonicated tissue and the organic solvent are placed in the container so that the lysate or sonicated tissue is completely submerged in the solvent. It is also noted that, regardless of the ratio of organic solvent to aqueous solution used to permit the glycans or other carbohydrates in the aqueous sample to be retained on the first porous solid support, once the carbohydrates are retained on the solid support, organic solvent is used to wash away any remaining aqueous solution to provide anhydrous conditions conducive to reducing the carbohydrates or labeling them by reductive amination.

Volumes of Organic Solvent to Reduce Concentration of Aqueous Solution

As noted in preceding sections, standard protocols for reducing glycans or other carbohydrates or for labeling them by reductive amination rely on drying down the glycan or carbohydrate prior to the reductive amination, as these procedures generally require anhydrous conditions. As also noted above, glycans released from glycoproteins by enzymatic digestion and carbohydrates in lysates or other biological samples are typically present in an aqueous solution and a drying step is typically necessary to provide the anhydrous conditions necessary for reduction or reductive amination to proceed.

In embodiments of the inventive methods, the drying down step, and thus the time needed to perform it, is eliminated by introducing an excess of organic solvent to the aqueous solution containing the glycan or other carbohydrate. As used herein, the phrase "excess of organic solvent" means an amount of organic solvent that reduces the ratio of aqueous solution to the organic solvent to a point at or which carbohydrates in the sample will be retained on a hydrophilic surface, or which will cause them to aggregate, precipitate, or both, so they can be retained on the first porous solid support by filtering the aggregated or precipitated glycans or carbohydrates through the first porous solid support.

In studies underlying the present disclosure, standard deglycosylation protocols were followed in which glycoproteins were subjected to enzymatic digestion in an aqueous solution, resulting in the release of glycans into the aqueous solution. Typically, the protocols resulted in 25-50 µl of aqueous solution containing the wholly or partially deglycosylated glycoprotein, the deglycosylation enzyme, glycans released from the glycoprotein, buffer salts, reductants, and other denaturants (consistent with its use elsewhere in this disclosure, this mixture is referred to in this section as the "starting aqueous solution sample"). A large excess of organic solvent, 675 µl, was then added to the starting aqueous solution sample, resulting in a solvent/solution mixture of roughly 19 parts organic solvent to 1 part starting aqueous solution sample (assuming an average of 35

μl of starting aqueous solution sample). A porous solid support of glass fibers was then contacted with the solvent/solution mixture, allowing glycans in the sample to be retained on the first porous solid support. Without wishing to be bound by theory, as the concentration of organic solvent averaged over 95%, it is believed that the glycans precipitated or aggregated and were retained on the glass fibers by filtration, although some hydrophilic interactions may have also contributed. Glycans immobilized on the solid support were then labeled by reductive amination while they remained immobilized on the first porous solid support, following which the labeled glycans were eluted from the first porous solid support for analysis.

While a ratio of 95% or more organic solvent to 5% or less aqueous solution was chosen in these initial studies to test the retention of the carbohydrates on the first porous solid support in the presence of a large excess of organic solvent to the starting aqueous solution sample, other studies were conducted using different ratios of organic solvent to aqueous solution and a different material, silica particles derivatized with aminopropyl, as the first porous solid support. These studies indicated that at least some carbohydrate were retained on the solid support at a 1:1 ratio of organic solvent to starting aqueous solution sample, but that a higher percentage of the carbohydrate present in the sample was retained on the solid support at higher ratios of organic solvent to aqueous solution. Ratios of organic solvent to aqueous solution that will result in more complete or complete capture of carbohydrates present in a particular sample is expected to vary somewhat depending on the particular organic solvent used and the particular material used as the first porous solid support. Persons of skill are familiar with solid phase extraction material and procedures used to capture carbohydrates and it is expected that the knowledge of solvents and materials useful in solid phase extraction procedures for carbohydrates provides the guidance needed for the practitioner to choose appropriate solvents and materials useful in embodiments of the inventive methods.

In light of these results, it is believed that concentrations of organic solvent from 70% to 100% are useful in allowing carbohydrates to be retained on the solid support, with each percent concentration over 75% being successively more preferred and concentrations of 80% or more being more preferred to concentrations of 75-79%. As noted above, the particular minimum ratio of organic solvent to aqueous solution that will allow carbohydrates to be retained or both on any particular solid support is expected to depend on the particular organic solvent and the particular solid support selected. Any particular ratio of organic solvent to aqueous solution, or concentration of organic solvent, for use with regard to a particular organic solvent and a solid support of any particular material can be readily tested by, for example, running two parallel sets of assays following the protocol set forth in the Examples, in which the first assay uses a 19:1 ratio or concentration of organic solvent to aqueous solution (the "known ratio" or "known concentration") and the second uses a particular ratio or concentration to be tested (the "test ratio" or "test concentration"). If analysis of the amount and types of glycans reduced or labeled using the test ratio or concentration is within an acceptable variation of the measurement of the amounts and types of glycans reduced or labeled in using the known ratio or concentration, than the test ratio or concentration is acceptable for use with reducing or labeling glycans using the particular solid support being tested. As different carbohydrates and different solid supports might require a higher ratio or concentration of organic solvent to aqueous solution, or might work well with a lower ratio or concentration, similar parallel assays can be used to determine ratios of organic solvent to aqueous solution suitable for use with any particular combination of carbohydrate to be labeled and of solid support to be tested to capture the carbohydrates in the solution. As persons of skill will appreciate, analysis of glycans attached to glycoproteins often requires testing to determine, for example, how best to deglycosylate a particular glycoprotein of interest, which may be more or less resistant to deglycosylation depending on factors such as the protein's tertiary structure, whether the glycans are accessible to the deglycosylation enzyme, and how resistant the glycoprotein is to denaturation to render the glycans accessible. Thus, the amount and type of testing described above is considered routine in this art.

While the discussion above has focused on determining ratios in which there is less organic solvent present compared to the amount of aqueous solution, mixtures in which the ratio of organic solvent to the aqueous solution is higher than 19:1, such as 20:1, 22:1, 23:1, 24:1, 25:1, 26:1, 27:1, 28:1 and 29:1, 30:1-39:1, or 40:1-49:1 are also expected to be useful. Ratios higher than about 25:1, however, increase the amount and cost of the reagents used and the size of the container needed to resulting mix of reagents, without necessarily adding to the retention of the carbohydrates on the solid support. Further, higher ratios may dilute the carbohydrates to the point a longer incubation period is required for them to come into contact with, and be retained on, the solid support. Thus, ratios of organic solvent to the aqueous solution higher than 49:1 are less preferred. It is believed to be preferable to use a ratio of organic solvent to aqueous solution sufficient to allow the glycans or other carbohydrates in the original aqueous solution sample to be retained on the solid support and then to wash the solid support with organic solvent to remove any remaining aqueous solution so that reduction or reductive amination can be conducted.

Containers Holding Solid Supports

As noted above, in typical embodiments, the glycans or other carbohydrates to be reduced or labeled by reductive amination are initially in an aqueous solution, which is then diluted by adding it to larger amounts of an organic solvent (or, conversely, by adding large amounts of an organic solvent to the aqueous solution containing the glycans or other carbohydrates). Conveniently, the resulting organic solvent/aqueous solution containing the glycans or other carbohydrates to be reduced or labeled is placed into a second container designed for this purpose. In typical embodiments, the container has a body having a length and two ends. In some embodiments, the two ends are disposed opposite each other along the length of the body of the container. The ends are each independently open or may independently be openable to allow the introduction of solutions and reagents at the first end and the exit of solutions and reagents at the second end. In some embodiments, the container is cylindrical. In some embodiments, the container is cylindrical, but narrows to a nozzle at the second end to facilitate capture of eluted labeled carbohydrates for analysis when they are eluted. In some embodiments, the container may an Eppendorf tube, a microfuge tube, or a centrifuge tube. Typically, such tubes have a first section that has an open or openable first end opening, a cylindrical body, connecting to a second section opposite the first end, which second section has a conical shape that narrows as it proceeds away from the cylindrical first part, until it reaches a second end. The second end can be open, but in some embodiments can be closable, allowing solutions in the container to incubate in the container when the bottom end is closed, but to allow solutions to flow out of the container when the second end is opened. For example the bottom end may be fitted with a cap or a removable cover to allow the user or an automated device to open the bottom end and allow a solution in the container to flow out. In other embodiments, the container can be generally cylindrical, conical, tetrahedral or cuboidal in shape. The containers may be shaped to be received into an apparatus designed to receive them, in which case they may be referred to as "cartridges."

In some embodiments, the second container is a well in a multi-well plate, and in preferred embodiments, each well of the multi-well plate is a container adapted for capturing and retaining carbohydrates, such as glycans, as described above. Such wells typically have a cylindrical body narrowing to a bottom section comprising an opening to allow solutions to exit the well. The exit at the bottom of the well is preferably narrower than the diameter of the well and can be a nozzle that projects from the bottom of the well, particularly where it is desired to use the plate in a system for automated collection of samples.

Whether the second container is a tube, a cartridge, or a well, it has a first porous solid support disposed between the top of the container and the exit. In some embodiments, the second container further has a second porous solid support disposed between the first porous solid support and the exit. In some preferred embodiments, the first porous solid support is a membrane or a monolith. In preferred embodiments, the first porous solid support is disposed just above the bottom of the container. In a well comprising a nozzle, the first porous solid support is preferably disposed just above the nozzle. In a further preferred embodiment, the second porous solid support is a hydrophilic material disposed between the first porous solid support and the exit. In embodiments in which the second porous solid support is, for example, comprised of beads, such as naked or derivatized silica beads, which may have a diameter smaller than that of the exit from the container, the beads or other second porous solid support can be held in place by conventional means, such as by having one or more porous compression frits, or by having a plastic retainer under the beads or other second porous solid support.

Solid phase extraction (SPE) cartridges and other devices containing hydrophilic polymers for retaining carbohydrates typically have a means for retaining the polymers within the devices. These means are typically selected to be non-reactive with the carbohydrates or reagents to which they are expected to be exposed and to permit fluids, such as wash solutions, to exit the device through the intended egress, such as a nozzle. Any of these conventional means can be used or adapted to retain the first or the second porous solid support in the inventive devices.

The reaction containers themselves are made from materials that are non-reactive with the reagents and solutions that will be used in them. Typically, the reaction containers are of plastic. Cartridges and containers for the SPE of carbohydrates are well known in the art and available from a number of vendors. The plastics or other materials used for SPE cartridges used to separate carbohydrates from other types of compounds, such as proteins, are suitable for use in the inventive methods and devices.

Whatever the shape, the container comprises a lumen which contains the first porous solid support and, in embodiments for use with APTS or other labels not very soluble in organic solvents, a second, porous hydrophilic solid support disposed downstream of the first porous solid support along the path the maker intends reagents to travel through the container from their introduction into the container through to their exit. The first and second porous solid supports are described further below.

In some embodiments, the reaction containers are designed so that the solutions used in the methods travel vertically through the container, allowing gravity to help move the solutions though the porous first solid support and, in embodiments with a second porous solid support, through that support as well. In some embodiments, the containers are designed so that solutions move the reagents through the container under pressure. For example, the methods can be used in microfluidic tubing or channels having a lumen by having the first solid support disposed in the lumen in a portion of the tubing or channel (thereby serving as the reaction container), and a second porous solid support in the same or in the lumen of a further section of channel or tubing disposed horizontally or vertically from the reaction chamber, with solutions flowed from the reaction chamber to the second solid support by fluid pressure gradient in the tubing or channel. In embodiments in which the second porous solid support is in a second section of tubing or channel, the lumen in which the reaction chamber is disposed is fluidly connected to the lumen of the tubing or channel in which the second porous solid support is positioned; in others, the two lumens might be separated by a valve or other means which permit the two lumens to be fluidly connected when desired.

First and Second Porous Solid Supports and Pore Sizes

The inventive methods contemplate the use of a first porous solid support to capture and retain carbohydrates present in a solution that is either neat organic solvent or a mixture of a high ratio of organic solvent to aqueous solution. In some embodiments, the inventive methods further contemplate use of a second porous solid support which can capture and retain labeled carbohydrates released from the first solid support in the presence of a solution with a lower ratio of organic solvent to aqueous solution.

The term "solid support" means that the support has a solid surface, but it is not necessary that the solid support be made of a single piece of the material from which it is made. The "solid support" can, for example, be composed of a plurality of derivatized silica beads which when grouped together and disposed across the second container provide a hydrophilic surface on which glycans or other carbohydrates can be retained. If the solid support is made of beads or similar particles of material, the beads may be compacted or retained in, for example, a plastic retainer, to retain the beads at the desired position in the second container. In such embodiments, the plastic retainer may be composed of a plastic ring sized to just fit across the lumen of the second container, attached to pieces of plastic cross hatched from the ring like a tennis racket with holes between the cross hatched pieces of plastic smaller than the diameter of the beads, thereby keeping them in place while allowing liquids to flow through. Similarly, the solid support can be made of glass fibers which can be disposed over and across one another to provide surfaces on which glycans or other carbohydrates can be retained. If needed, the glass fibers can be retaining in place by a plastic retainer like the one described above. In embodiments in which a second porous solid support is not used, the beads, glass fibers, or other embodiments in which the solid support is not a single structure can be packed into a bed at the bottom of the second container. Beads and other particles can be retained by, for example, narrowing the walls of the container to a diameter below the diameter of the beads or particles, or by positioning a suitable retainer with cross hatched pieces which leave holes or openings too small for the beads or particles to pass through.

In some embodiments, the hydrophilic material is shaped into a membrane or a monolith which is rigid as well as porous. The membrane or monolith can then be shaped into a shape fitting precisely into the lumen of the second container and filling the cross section of the lumen at the desired position.

Whether the first porous solid support is of beads, particles, a membrane, or a monolith, it is positioned at the desired point in the container across the entire cross section of the container's lumen so that solutions or solvents in the container must pass through the first porous solid support before exiting. If the second container narrows from a cylindrical section to a conical section, as in a typical Eppendorf tube, the beads, particles, membrane or monolith can, for example, be sized to completely cover the area of the bottom of the cylindrical section and be retained in position by the narrowing below of the wall of the container to form the conical section. Similarly, if the second container is the cylindrical portion of a well of a multiwell plate, and the well has a nozzle at the bottom with an opening allowing solutions to exit the well when desired, the beads, particles, membrane or monolith can be sized to completely cover the area of the bottom of the cylindrical section of the well and be retained in position by the narrowing of the wall of the well form the nozzle section below the membrane or monolith.

In embodiments in which hydrophilic materials are used for the first porous solid support, and the glycans or carbohydrates are not monosaccharides or very small, the pore or opening size can be larger than in the embodiments discussed below, so long as the pores or openings force the glycans or other carbohydrates to come into contact the hydrophilic material as the organic solvent/starting aqueous solution sample flows through the first porous solid support. The glycans or other carbohydrates will tend to interact with, and be retained on, the hydrophilic material of the solid support when in an organic solvent that is in a concentration of 80% or more organic solvent to 20% or less aqueous solution.

As used herein, the terms "porous" and "permeable" used in describing a solid support are intended to convey that the solid support allows solvents and solutions to filter gradually through it. All solid supports described in this disclosure are porous solid supports unless otherwise specified or required by context. It should be noted that the porous solid supports may in some embodiments rest on or be held in place by, for example, fittings, narrowing of the container walls, or internal structures of the container in which they are disposed. Such fittings, narrowings, or internal structures are solid and may retain or support the first and second porous solid supports, but they are typically made of the same material as that of the reaction container and are not intended to be considered as being a first or a second porous solid support as those terms are used in this disclosure.

Materials for the First Porous Solid Support

As discussed in the Introduction, most glycans and other carbohydrates, other than monosaccharides and other carbohydrates that are only weakly hydrophilic, will be retained on solid hydrophilic surfaces when organic solvent is added to the starting aqueous solution sample to a point at which the concentration of organic solvent is 80% to 95%. Accordingly, in many embodiments, the first porous solid support can be any hydrophilic material that is not chemically reactive with the reagents to be used, which presents a solid surface and which can be fashioned to allow liquids to percolate through it. A number of materials are currently used in cartridges and columns to retain carbohydrates in SPE procedures and can be used in embodiments of the inventive methods. For example, the solid support can be made of cellulose, glass (such as glass fiber), alumina, functionalized surfaces containing diol, aminopropyl, amide, cyanopropyl, ethylenediamine-N-propyl, or a porous hydrophilic material known to retain carbohydrates in an organic solvent. In some embodiments, the solid support is made of silica beads, and in some embodiments, the silica beads are derivatized with aminopropyl, diol, or carbamoyl groups. The first porous solid support preferably does not have carboxyl groups available on the surface. As used herein, the terms "functionalized" and "derivatized" are equivalent and mean that the surface of the material forming the body of the solid support is covalently bonded to molecules of one of the functional groups (e.g., aminopropyl, diol, carbamoyl) listed or, in some embodiments, to molecules of two or more of these functional groups (e.g., both diol molecules and carbamoyl molecules are covalently attached to the surface of the material of the first porous solid support). In some preferred embodiments, the material is silica. The molecules of the functional groups are available to interact non-covalently with carbohydrates when contacted with them under conditions (such as temperature and pH) that allow interaction. Solid phase extraction of carbohydrates and other polar, hydrophilic molecules has been performed in the art for years and conditions for performing SPE is generally suitable for use in conducting embodiments of the inventive methods. It is expected that persons of skill are familiar with the conditions under which SPE is performed.

In some embodiments, the organic solvent is to be present at a concentration above 95%. These embodiments permit capturing monosaccharides or other glycans or carbohydrates that are only weakly hydrophilic and which do not precipitate well in organic solvents when water is present in concentrations above 5%. Or, the practitioner may be wish to capture and analyze larger glycans or carbohydrates present in a sample, which could be captured by the hydrophilic materials described above, but also wishes to capture monosaccharides which might not be retained on the solid support when concentrations of organic solvent of 95% or lower are used. For these embodiments, a larger range of materials may be used for the first porous solid support, including both the materials named in the preceding paragraph and others that are not hydrophilic, as it is expected that glycans or other carbohydrates will come out of solution and to aggregate, precipitate, or both, allowing them to be captured on the first porous solid support by physical filtration, rather than relying on hydrophilic interactions between the glycans or other carbohydrates and the material of the solid support. The first porous solid support in these embodiments may therefore be any material that is (a) solid, (b) not reactive with the reagents to be used, (b) capable of being shaped to stay in place within the second container and fill the cross section of the container's lumen so that the solutions or solvents have to filter through pores or openings in the material, and either (d) can have pores or other openings of 10 microns to 0.05 microns made through it, or (d') which can be produced in beads or other particles that can be packed into a bed or a retainer and have pores or openings within that size range. Thus, the hydrophilic materials described above can be used, but so can, for example ceramic filters with appropriate pores sizes. Any particular material can be tested for its suitability for use in these embodiments by the assay taught in the section on testing combinations of organic solvents and materials for the solid support.

In studies underlying the present invention using polyethylene ("PE") as the first porous solid support, it was determined that glycans were efficiently captured if the pore size of the first porous solid support was ten microns or smaller. Some studies underlying the present invention used glass fiber with a pore size of approximately 0.7 microns, which was found to work well. It is expected that smaller pore sizes can be used so long as the pores are not so small that solvents and solutions do not filter through so slowly that it unduly slows the procedure or even prevents the solvents or solutions from exiting the container. Any particular pore or opening size can be readily tested to see if solvents and unwanted reagents filter through the first or second porous solid support, respectively, in a time deemed reasonable by the practitioner. Persons of skill will further appreciate that the solid support should have a large plurality of pores or openings to facilitate flow of solvents and unwanted reagents through the solid support, as having only a few pores or openings will slow their passage through the solid support without providing any benefit in separating and immobilizing the glycans or other carbohydrates on the solid support. As SPE cartridges for separating carbohydrates have been available for years, it is expected that persons of skill can use the pore size and composition of such cartridges as guidance for determining appropriate materials and pore sizes for use as porous solid supports in the inventive methods and devices.

In some particularly preferred embodiments, the material used for the first porous solid support is PE, as it is inexpensive, can be produced in suitable thicknesses with pores of suitable sizes, and can be readily shaped into a shape that will stay in position within a container, cartridge, well or column and fill the cross section of the container's lumen. In preferred embodiments, the pore size of the PE is 10 microns to 0.25 microns. In preferred embodiments, the PE may have pores or openings of 10, 9, 8, 7, 6, 5, 4, 3, or 2 microns, 1 micron, or 0.5 microns, or any size within that range. In some preferred embodiments, the PE is a monolith. In some embodiments, the PE is a membrane.

For analytical uses, the total volume of solutions used is typically 1 mL. For preparative scale uses, the volumes of solutions used might be a liter or more and the thickness of the material can be considerably larger. The first porous solid support preferably has a plurality of pores, which are small enough to prevent aggregated or precipitated glycans or other carbohydrates from passing through, but large enough to allow liquids and dissolved reagents to pass through. (Appropriate pore sizes are discussed in the preceding section.) Persons of skill are expected to be able to select materials appropriate for the first porous solid support.

It was originally thought that the glycans or other carbohydrates bind to the first solid support in the presence of the organic solvent or mixture of a high ratio of organic solvent to aqueous solution in which the carbohydrates are provided to the first solid support. Without wishing to be bound by theory, it is now thought that, in embodiments using hydrophilic materials for the first porous solid support, and organic solvents in concentrations of 80%-95%, the glycans or other carbohydrates are retained on the support by hydrophilic interactions, while at higher concentrations of organic solvent, the glycans or other carbohydrates come out of solution and aggregate or precipitate. It is further thought that these aggregates or precipitates, or both, are collected on the first porous solid support largely due to filtration.

Other interactions between the carbohydrates and the first porous solid support may, however, be at play in the presence of the solvent/solution mixture depending on the chemical nature of the porous solid support. For example, there may be as ionic interactions or hydrogen bonding present in the pH, temperature, and salt concentrations under which the solvent/solution mixture is provided to the first solid support, and to which the solid support and carbohydrates will be further subjected during later steps of the inventive methods. Whatever the mechanism of action, the result is that most or all of the glycans or other carbohydrates in the organic solvent or mixture of a high ratio of organic solvent to aqueous solution are non-covalently retained on the first porous solid support rather than passing through when in that solvent or mixture of a high ratio of organic solvent to aqueous solution. Without wishing to be bound by theory, it is believed that embodiments using following Workflow 1A retain carbohydrates on the first porous solid support in step 3 by filtration and retain them during the wash in step 6 by filtration, that embodiments following Workflow 1B retain carbohydrates on the first porous solid support in step 3 by filtration and capture and retain them on the second porous solid support during the wash of step 6 by hydrophilic interaction, and that embodiments using Workflow 1C retain carbohydrates on the first porous solid support in step 3 by hydrophilic interaction and retain them during the wash in step 6 by hydrophilic interaction.

Graphitized carbon was initially thought to be suitable as a first solid support for use in the inventive methods and kits. Graphitized carbon is, however, unsuitable for the first porous solid support, for several reasons. First, as noted above, the first porous solid support should not be one that will retain the glycans or other carbohydrates in an organic solvent or a solvent mixture that consists primarily of an organic solvent. Graphitized carbon will not retain glycans or other carbohydrates when the carbohydrates are in solution containing a high ratio of organic solvent to aqueous solution. Second, some embodiments of the inventive methods contemplate that the glycans or other carbohydrates are in a solution also containing aglycosylated protein from which the glycans or other carbohydrates have been released by enzymatic digestion, and may also contain the deglycosylation enzyme, which is also a protein. It is believed that graphitized carbon will retain aglycosylated protein and enzyme present in the solution and that the retained protein will clog the pores of the solid support. Graphitized carbon should therefore not be used for either the first or the second porous solid support.

In some embodiments, the first porous solid support is made of glass. Preferably, the glass is in a form that has a high amount of surface area to facilitate retention of carbohydrates in the solvent/solution mixture and preferably is in a form through which the mixture can be flowed to facilitate such capture. For example, the glass can have a plurality of small holes allowing fluids to filter through it or be in form of beads or particles. In some preferred embodiments, the glass is in the form of glass fibers. In some embodiments, the glass fibers can be loose. In some embodiments, the glass fibers can be woven. In embodiments in which the glass fibers are loose, the fibers will typically be used in conjunction with an underlying structural support that holds the fibers in the container while solvents, solutions, and unwanted reagents are flowing through. In these embodiments, the structural support is disposed between the glass fibers and the opening through which the solvents, solutions and unwanted components exit from the container.

In some embodiments, the first porous solid support is made of a form of aminopropyl. Various forms of aminopropyl are known in the art to be useful for separating carbohydrates and several are commercially available. For example, aminopropyl AP (NH2) HPLC columns for separating carbohydrates are available from Separation Methods Technologies, Inc. (Newark, Del.). APHERA™ NH2 HPLC columns are sold by Sigma-Aldrich Co. (St. Louis, Mo.) Aminopropyl silanes are used in the art for HILIC separation of sugars. It is expected that persons of skill are familiar with the various ways in which aminopropyl is used for separating carbohydrates in procedures such as HPLC and HILIC and can select suitable forms of aminopropyl for binding carbohydrates, such as N-glycans, in embodiments of the inventive methods in which an aminopropyl is to be employed.

In some embodiments, the first porous solid support is made of cellulose. Cellulose can be used in sheets, but it is commonly used in solid phase extraction as a microcrystalline powder and that form is preferred as it provides a larger surface area for binding the carbohydrates. As practitioners will appreciate, use of solid phase supports that are in the form of powders, nanoparticles, or other small particles will typically be used in conjunction with a filter or other structure that allows solvents, solutions, and unwanted reagents to flow through upon elution while the powder or nanoparticle or other small particles are retained in the container. In these embodiments, the filter or other structure is disposed between the powder, nanoparticles, or other small particles and the opening through which the solvents, solutions and unwanted components exit from the container.

In some embodiments, the first solid support can be a porous hydrophilic material that preferentially retains carbohydrates over proteins, buffer salts, reductants, or other reagents known to be present in a particular mixture from which the carbohydrates are to be separated.

Materials for Second Solid Support

As described above, when the carbohydrates on the first porous solid support are reduced by reductants that are not very soluble in organic solvent, or are labeled by reductive amination with APTS or other labels that are not very soluble in organic solvent, removal of the reductant or of excess label requires use of a solution of organic solvent mixed with some water, at a concentration of water that will cause the reduced or the labeled carbohydrates to come off the first porous solid support. Such washes will typically be 60-90% organic solvent to 40-10% aqueous solution, with about 75-85% organic solvent to 25-15% aqueous solution being preferred and 80%-85% organic solvent to 20-15% aqueous solution being preferred (any particular percentage of organic solvent chosen by the practitioner will of course be matched by the percentage of aqueous solution needed to bring the mixture up to a total of 100%). In these cases, a second porous solid support is used that can capture and retain the labeled carbohydrates in the presence of such a solution. Thus, in some embodiments, the invention provides containers that have a first porous solid support as described above, and a second porous solid support disposed along the path the solutions flow between the first porous solid support and the opening though which the reductant or labels exit the container.

As the name implies, the second porous solid support is porous, and is preferably of a hydrophilic material, such as resins typically used for HILIC separations of carbohydrates or for solid phase extraction (SPE) of carbohydrates. It is contemplated that materials used in HILIC separations of carbohydrates and in SPE extraction of carbohydrates are generally suitable for use in the second porous solid support. SPE is widely used in the art and teachings about its use abound, as exemplified by Thurman and Mills, SOLID-PHASE EXTRACTION: PRINCIPLES AND PRACTICE, John Wiley & Sons Inc. (New York, N.Y., 1998), N. Simpson, Solid-Phase Extraction: Principles, Techniques, and Applications, Marcel Dekker Inc. (New York, N.Y., 2000), and Waters Corp., BEGINNER'S GUIDE TO SPE: SOLID-PHASE EXTRACTION, John Wiley & Sons Inc. (New York, N.Y., 2014). Accordingly, it is expected that persons of skill can readily select materials appropriate for use as the second porous solid support.

Examples of porous hydrophilic materials suitable for the second porous solid support include: cellulose, glass, alumina, aminopropyl, or silica modified with diol, cyanopropyl, ethylenediamine-N-propyl, amide (carbamoyl), aspartamide, cyclodextrin, triazole, diethylaminoethyl, or combinations of two or more of these materials.

In some preferred embodiments, the second porous solid support is of silica beads or particles that are covalently bonded with carbamoyl groups. In some particularly preferred embodiments, the spherical silica beads or particles that are covalently bonded with carbamoyl groups are Amide-80. In preferred embodiments, the Amide-80 beads or particles are 3-60 microns in size, more preferably 5-50 microns in size and more preferably about 30 microns in size, with about here meaning ±2 microns. The second porous solid support captures any reduced or labeled glycans or other carbohydrates that come off the first porous solid support in the presence of the organic solvent/water wash solution described in the preceding paragraph.

It is further contemplated that the material used for the second porous solid support will release the retained reduced labeled carbohydrates upon being washed with an aqueous solution, such as phosphate buffered saline (for clarity, it is noted that the aqueous solution that elutes the reduced or labeled carbohydrates from the second porous solid support in this step differs from the mixture of organic solvent/ aqueous solution used to wash excess reductant or excess label off the first porous solid support as it does not contain the about 80% concentration of organic solvent of that wash. Typically, no organic solvent is present in the wash used in this step.

Configuration of the Materials of the First and Second Solid Supports

As noted, the first and the second solid supports are porous, to allow the solutions to filter through them, allowing the carbohydrates in the solution to be captured and retained. The material selected for the first porous solid support and for the second porous solid support either is in a configuration, such as being woven to permit the solvent/ solution to contact a large surface area of the material, or has a plurality of pores or opening that allow the same thing. Preferably, neither solid support is in the form of magnetic beads. As the inventive methods contemplate that the first and second solid supports are disposed in stationary positions within the second container and do not move or need to move, use of magnetic beads would add costs without providing advantages. Accordingly, they are not preferred for use in the inventive methods or devices.

In some embodiments, the first or second porous solid support, or both, is a membrane. In some embodiments, the first or second porous solid support, or both, is a monolith. In some embodiments, the first or the second porous solid support, or both, may be in the form of a resin, particles, or powder. In these embodiments, the resin, particles or powder will typically be retained in the second container by a structural support to prevent the resin, particles or powder from exiting the second container as the solutions and solvents flow through them. In some embodiments, the first or second porous solid support, or both, is in the form of a packed bed, which is retained in the container by the design of the container or other structural support. In preferred embodiments, the first or second porous solid support is both porous and rigid. In some embodiments, the first or second porous solid support, or both, may be disposed in a microfluidic channel. In embodiments in which the first or the second porous solid support, or both, is in a form in which it would not stay in place in the container, the container may further comprise have a structure or an insert to keep the first or second porous solid support, or both, in the desired position within the container. For example, the container may be formed with an internal piece extending across its width with holes or other openings sized not to permit the material of the first or of the second porous solid support, or both, to move outside of the intended position, but large enough to permit flow of solvents, solutions, and reagents. Alternatively, the container may include one or more structures, such as frits, disposed between the first or second porous solid support, or both, to retain the first or of the second porous solid support, or both, in the intended position(s). The structure or frit can itself be positioned in an annular ring or other structure shaped and sized to fit within the sides of the container, and the annular ring or other structure may for example, be sized and shaped to mate to a flange on the interior of the container. In some embodiments, the ring or other structure may secure to the flange or to structures on the interior of the container to hold the annular ring or other structure (and the filter attached to the ring or other structure) in the desired position. The ring or other structure may for example sized to mate to, for example, a matching slot or recess around the interior of the container or can have prongs or other protrusions from the ring or other structure to mate into matching slots disposed in the interior. In some embodiments, the ring or other structure can secure to the container by snap fit. For example, the ring or other structure may have a plurality of protrusions which snap fit into matching recesses in the wall of the container. Alternatively, the ring or other structure can be placed into the container and then fixed to the wall in the desired position by adhesive or by ultrasonic welding.

Flow of Solutions Through the First Porous Solid Support and, Where Applicable, Second Porous Solid Support It is contemplated that carbohydrates will be retained on the first porous solid support while the solvent/solution mixture, which may further include unwanted reagents such as buffer salts, deglycosylation enzyme, deglycosylated glycoprotein and the like, flows through the solid support. The carbohydrates on the first solid support can then be washed with organic solvent (the same or different from the organic solvent used in the mixture with the aqueous solution) to remove any remaining aqueous solution, and reductive amination conducted. Persons of skill will appreciate that the carbohydrates can be retained the first solid support in a matter of seconds, but it is not desirable for the carbohydrates to flow past the first solid support so quickly (for example, less than 1 second) that retention does not have time to occur, nor so slowly (for example, more than 15 minutes) that unnecessary time is added to the protocol. Flow speeds through the container therefore should be slow enough for the carbohydrates to have the opportunity to be retained on the solid support, but fast enough to avoid delays that add unnecessary time to the workflow. Persons of skill are familiar with selecting materials, such as for cartridges used in solid phase extraction protocols, with pore sizes and other characteristics resulting in a desired flow speed, as well as with the use of various procedures, such as positive pressure, centrifugation, or use of a vacuum manifold, for increasing the flow rate of liquids over or through a solid support. It is expected that practitioners are well familiar with extracting carbohydrates from a sample using solid phase extraction procedures by choice of material, pore sizes, and flow rates used in the extraction and that this familiarity provides ample guidance regarding choices of material for the first solid support, for the pore size, and for flow rates for use in flowing the solvent/solution mixture through the solid support in various embodiments of the inventive methods. Similar considerations can be used to determine appropriate sizes for pores or openings in the second porous solid support in embodiments in which one is present.

Labels

As noted in the Background, reductive amination and labeling with 2-AB was disclosed in co-owned U.S. Pat. No. 5,747,347, which issued in 1998. Reductive amination has been used extensively for labeling glycans and other carbohydrates in the two decades since the '347 patent issued, and it is assumed practitioners are familiar with procedures and conditions for labeling carbohydrates by reductive amination.

In general, any label or dye suitable for labeling carbohydrates by reductive amination can be used for labeling glycans or other carbohydrates in the inventive methods. Conveniently, the label is a fluorophore, such as 2-AA (anthranilic acid) or 2-AB (2-aminobenzamide). In some preferred embodiments, the label is 2-AB. In some preferred embodiments, the label is 2-AA. In some preferred embodiments, the label is APTS (8-aminopyrene-1,3,6-trisulfonic acid, CAS No. 196504-57-1). In some preferred embodiments, the label is procainamide hydrochloride (CAS No, 614-39-1). In some embodiments, the label contains a primary amine group that will react with the carbohydrate reducing end by reductive amination and either a fluorescent property, a chromophoric moiety, or a detectable charge. In some embodiments, the label is a chemical moiety that has a detectable charge.

Reductants

Reductants are used in embodiments of the methods when the desire is to reduce a glycan or other carbohydrate without labeling it, and in embodiments in which the glycan or other carbohydrate is to be labeled by reductive amination. Use of reductants both in reducing glycans or other carbohydrates and in reductive amination is well known in the art and will accordingly be described only briefly here. Reductants suitable for use in reductive amination of glycans include sodium cyanoborohydride and picoline borane. The reductant is typically in an organic solvent such as DMSO. Tetrahydrofuran (THF), which sometimes used as an organic solvent for reductants, is not compatible with plastic, and it should not be used as the organic solvent for the reductant in embodiments in which the reaction container or any components to be used in the reaction container, such as an internal support for holding the second porous solid support in place, is made of plastic. The solution containing the solvent and the reductant is typically added to the solution containing the label. The reductant concentration is typically 0.5 to 2M in the final mixture.

Reducing Glycans or Other Carbohydrates Without Labeling Them

The reductants and concentrations noted in the preceding paragraph can be used to reduce the glycans or other carbohydrates in the absence of a label. Reduction of glycans or other carbohydrates is routinely practiced in the art and it is expected that practitioners are familiar with appropriate solvents and concentrations. Appropriate reductants and concentrations are discussed in the preceding section. Once the glycans or other carbohydrates have been reduced, they can be eluted from the first porous solid support (or from the second porous solid support in embodiments in which the second porous solid support is used) by washing the support as described in the next section.

Eluting Retained Carbohydrates from the First Porous Solid Support

Once any excess reductant or excess label has been removed from the reduced or labeled glycans or other carbohydrates retained on the first porous solid support, the retained, reduced or labeled glycans or other carbohydrates are eluted from the first porous solid support by washing the support with an aqueous solution, which redissolves the aggregated or precipitated glycans or other carbohydrates. Aqueous solutions to which salts have been added are preferred. Combinations of solutions can also be used. The aqueous solution may comprise up to 20% organic solvent or be only of water or buffer solution. Any particular solution or combination can be readily tested for its suitability in eluting carbohydrates from a solid support made of any particular material by performing parallel assays, as discussed above.

Eluting Carbohydrates from the Second Porous Solid Support

As discussed in preceding sections, if the first porous solid support chosen is non-hydrophilic and the glycans or other carbohydrates have been reduced by reductants that are not very soluble in organic solvent, or have been labeled with APTS or another dye that is not very soluble in organic solvent, the glycans or other carbohydrates will come off the first porous solid support in the organic solvent/aqueous solution wash used to remove the excess reductant or label. Glycans or other carbohydrates coming off the first porous solid support will be captured on the hydrophilic second porous solid support. Once the excess reductant or excess label has been washed from the reaction container, the reduced or labeled glycans or other carbohydrates can be eluted from the second porous solid support using one or more aqueous solutions as described in the preceding section.

Kits

In some embodiments, the invention provides kits for immobilizing glycans or other carbohydrates on a first porous solid support and reducing or labeling by reductive amination on the glycans or other carbohydrates while they remain immobilized on the first porous solid support. In some embodiments, the kits provide a container containing, in order, a first opening for introducing solutions, a first section for receiving mixtures comprising a glycan or carbohydrate of interest, a first porous solid support, a second section, in which is disposed a hydrophilic second porous solid support, and a second opening, through which solutions can exit the container.

Conveniently, the first section between the first opening and the first porous solid support is sized to accept the volume of the mixture of organic solvent and starting aqueous solution sample used in the intended analytical or preparative scale reductions or labeling procedures. In preferred embodiments, the first porous solid support is non-hydrophilic. In some of these embodiments, the non-hydrophilic first porous solid support is made of polyethylene, nylon, polyvinylidene fluoride, or polypropylene. In preferred embodiments, the first porous solid support has pores or openings 10 microns or less in width, allowing mixtures of organic solvent and starting aqueous solution sample to filter through the first porous solid support. In some preferred embodiments, the first porous solid support is a monolith or a membrane disposed across and filling the cross section of the container so that mixtures flowed into the first section of the container have to filter through the first porous solid support. In other embodiments, it can be composed of not a single solid piece, but a collection of pieces, such as fibers, beads or particles. First porous solid supports composed of a collection of pieces, such as glass fibers or silica beads, can be retained at the desired position in the container by standard means, such as having the pieces disposed on a retainer, such as a plastic insert, or an internal cross hatching of the container in which the cross hatches are smaller than the size of the pieces.

In some embodiments, the container is a cartridge or a tube. In some embodiments, particularly for automated analyses, the container is a well in a multi-well plate. The exit at the bottom of the well can be a nozzle or the bottom of the well can narrow to facilitate eluting solutions exiting the well into desired receptacles. For clarity, it is noted that the container provided in the kits serves as the "reaction container" described in the inventive methods, as the sample containing the glycans or other carbohydrates to be reduced or labeled will typically be mixed with organic solvent in a separate container prior to use of the kits.

As noted, the container in the inventive kits further contains a hydrophilic second porous solid support disposed between the first porous solid support and the second opening. As with the first porous solid support, the second porous solid support is disposed across and filling the cross section of the second section of the container so that fluids containing glycans or other carbohydrates that come off the first porous solid support have to contact and filter through the second porous solid support. In some embodiments, the second porous solid support is a monolith or a membrane. In other embodiments, the second porous solid support is composed of not a single solid piece, but of a collection of pieces, such as fibers, beads or particles. The second porous solid support can be kept from moving towards the second opening by being disposed on a retainer, membrane, or filter. In some embodiments, both the first and the second porous solid supports each have a retainer, membrane, or a filter holding them in their respective places within the container. In some embodiments, in which the second porous solid support is composed of beads or particles, the walls of the container may narrow as they near the second opening, for example, forming a nozzle on the bottom of a well, to a size below the diameter of the beads or particles, preventing the beads or particles from exiting the container through the second opening. Other means known in the art for retaining beads or other materials within a SPE cartridge or other separation device can also be used. The choice of a particular means for retaining the first or the second porous solid supports, or both, is not critical so long as it permits the exit of solutions from the container when desired and is not reactive with the reagents expected during its use. Either the first opening, the second opening, or both, can have a removable cover.

The kits may include one or more deglycosylation enzymes, one or more denaturants (such as sodium dodecyl sulfate), and preferably contain one or more labels for reductive amination. The labels can be, for example, 2-AA, 2-AB, APTS, procainamide hydrochloride, or two or more of these. The kit may contain a reductant, which may be in powder form or which may dissolved in an organic solvent.

The reductant can be, for example, sodium cyanoborohydride or picoline borane. The kits may further contain printed instructions on how to immobilize glycans or other carbohydrates on the first porous solid support and how to reduce them or to label them by reductive amination while they remain immobilized on the first porous solid support in the container, and how to elute the reduced or labeled glycans or other carbohydrates from the container depending on the reductant or label used in the procedure.

EXAMPLES

Example 1

This Example sets forth abbreviations for some of the reagents used in exemplar workflows of deglycosylation and labeling procedures described in the Examples below.

"PNGase F mix": a 1:1 mix of PNGase F (~1 mg/ml) and 750 mM ammonium bicarbonate pH 8.0 buffer.

"2-AB": 2-aminobenzamide

"2-AB labeling mix": 2 mg/ml 2-aminobenzamide, 40 mM cyanoborohydride, 200 mM acetic acid in 90:10 acetonitrile:DMSO.

"DTT": Dithiothreitol.

"APTS": 8-aminopyrene-1,3,6-trisulfonic acid.

"APTS labeling mix": 2 mg/ml 8-aminopyrene-1,3,6-trisulfonic acid, 40 mM cyanoborohydride, 200 mM acetic acid in 90:10 acetonitrile:DMSO.

Example 2

This Example sets forth an exemplar workflow for N-glycan release by enzymatic digestion and labeling with 2-AB using an exemplar solid support.

N-Glycan Release and Preparation Step

Twenty μl of 2 mg/ml glycoprotein are denatured at 90° C. for half an hour in the presence of DTT (1 μL, 550 mM). The solution is cooled and 2 μl of PNGase F mix is added and incubated for 16 hours at 37° C. to release N-glycans from the glycoprotein.

N-Glycan Precipitation and Cleanup Step

The mixture (approximately 23 μl) is mixed with 600 μl of acetonitrile and loaded onto a glass fiber membrane mounted in a 1 mL column. In these conditions, N-glycans precipitate on the glass fiber membrane, while contaminants like denaturant are washed away with the solvent. Additional washes with acetonitrile can be performed to reduce the presence of contaminants whose retention on the glass fiber membrane is not desired.

N-Glycan Labeling

Twenty five μL of 2-AB labeling mix is added to the glass fiber membrane. The labeling reaction is permitted to proceed for one hour at 70° C.

Reactant Excess Wash and Elution Step:

If desired, the solid support can be washed with acetonitrile to remove any excess dye. Purified labeled glycans can then be eluted from the solid support using water.

Analysis Step

Labeled N-glycans eluted from the membrane are then analyzed. For example, 1 μl of eluted N-glycans can be analyzed by providing them to a high performance liquid chromatography (HPLC) instrument to separate the glycans and then to a device which detects and measures fluorescence of the separated glycans.

Example 3

This Example sets forth an exemplar workflow for labeling free oligosaccharides with APTS, using an exemplar cellulose solid support.

N-Glycan Release and Preparation Step

Twenty μl of 0.5 mg/ml maltodextrin in aqueous solution are mixed with 600 μl of acetonitrile, an organic solvent, and loaded onto a cellulose membrane mounted in a 1 mL column. In these conditions, free glycans aggregate or precipitate on the solid support, while other components and water are washed away with the organic solvent. Washes with acetonitrile can be performed to further reduce the presence of any water remaining on the support after the initial acetonitrile/aqueous solution drains from the container.

N-Glycan Labeling

Fifteen μL of the APTS labeling mix are added to the cellulose membrane. The labeling reaction is permitted to proceed for one hour at 70° C.

Reactant Excess Wash and Elution Step:

If desired, the solid support can be washed with 85% acetonitrile/15% water to remove any excess dye. Purified labeled oligosaccharides can then be eluted from the porous solid support using water.

Analysis Step

Following elution, labeled oligosaccharides are analyzed. For example, 1 μl of eluted sample can be analyzed by providing it to a high performance liquid chromatography (HPLC) instrument to separate the labeled oligosaccharides and then to a device which detects and measures fluorescence to measure the fluorescence of the labeled oligosaccharides.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A device for reducing or labeling by reductive amination carbohydrates provided to said device in an organic solvent, said device comprising: a reaction container having a body with (a) a first opening, (b) a first section with a first lumen having a first cross section having an area and a first diameter, wherein said first lumen is fluidly connected to said first opening, (c) a second section having a second lumen with a second cross section having an area and a second diameter, wherein said second lumen is fluidly connected to said first lumen of said first section, (d) a second opening fluidly connected to said second lumen, (e) a first porous solid support for capturing said carbohydrates originally provided to said device in said organic solvent, said first porous solid support disposed between said first opening and said second opening, filling said area of said first cross section of said first lumen, and fluidly connected to said first lumen and said second lumen across the entire area of said first cross section of said first porous solid support being (1) made of a non-hydrophilic material or having a surface of a non-hydrophilic material, or (2) made of a hydrophilic material, and (f) a second porous solid support, configured for capturing said carbohydrates when eluted from said first porous solid support following their being reduced or labeled by reductive amination while immobilized on said first porous solid support, said second porous solid support composed of a hydrophilic material or having a surface of hydrophilic material, wherein said second porous solid support is disposed between said first porous solid support and said second opening and fills said area of said first cross section or of said second cross section.

2. The device of claim 1, wherein said first diameter of said first section of said body of said reaction container is wider than said second diameter of said second section.

3. The device of claim 1, wherein said first porous solid support is disposed in said first section of said reaction container and said second porous solid support is disposed in said second section of said reaction container.

4. The device of claim 1, wherein said reaction container is a tube or cartridge.

5. The device of claim 1, wherein said reaction container is a well in a multiwell plate.

6. The device of claim 5, wherein said second section of said well is a nozzle protruding from a bottom of said well.

7. The device of claim 6, wherein said second porous solid support is disposed in said nozzle.

8. The device of claim 1, wherein said reaction container is within a microfluidic apparatus.

9. The device of claim 1, wherein said first porous solid support is made of a non-hydrophilic material or has a surface of a non-hydrophilic material.

10. The device of claim 9, wherein said non-hydrophilic material of said first porous solid support has pores or openings of 10 microns or less in width.

11. The device of claim 9, wherein said non-hydrophilic material is polyethylene and has pores or openings of 10 microns or less in width.

12. The device of claim 1, wherein said first porous solid support is composed of a hydrophilic material.

13. The device of claim 12, wherein said hydrophilic material is made of (a) glass, (b) cellulose, (c) silica, (d) a surface covalently linked to a plurality of aminopropyl, diol, carbamoyl groups, Zwitterionic groups, or a mixture of two or more of said groups, or (e) silica covalently linked to a plurality of aminopropyl, diol, or carbamoyl groups, or a mixture of two or more of said groups.

14. The device of claim 13, wherein said first porous solid support is composed of glass fibers.

15. The device of claim 1, wherein said hydrophilic material of said second porous solid support is made of (a) glass, (b) cellulose, (c) silica, (d) a surface covalently linked to a plurality of aminopropyl, diol, carbamoyl groups, Zwitterionic groups, or a mixture of two or more of said groups, or (e) silica covalently linked to a plurality of aminopropyl, diol, or carbamoyl groups, or a mixture of two or more of said groups.

16. The device of claim 15, wherein said hydrophilic material of said second porous solid support is composed of glass fibers.

17. The device of claim 15, wherein said hydrophilic material of said second porous solid support is silica in the form of beads or particles.

18. The device of claim 17, wherein said beads or particles are covalently linked to a plurality of carbamoyl groups.

19. The device of claim 18, wherein said silica beads or particles having a plurality of carbamoyl groups is Amide-80.

20. The device of claim 1, wherein said first porous solid support is polyethylene having pores or openings 10 microns or less in width and said second porous solid support is composed of silica beads or particles covalently linked to a plurality of carbamoyl groups.

21. The device of claim 20, wherein said silica beads or particles having a plurality of carbamoyl groups is Amide-80.

22. The device of claim 1, wherein said second opening has an openable cover to retain solutions in the reaction container until their exit is desired.

23. A kit for reducing carbohydrates or labeling carbohydrates by reductive amination, comprising:
(a) a reaction container having a body with (a) a first opening, (b) a first section with a first lumen having a first cross section having an area, wherein said first lumen is fluidly connected to said first opening, (c) a second section having a second diameter and a second cross section having an area, with a second lumen with a cross section having an area, wherein said second lumen is fluidly connected to said first lumen of said first section, (d) a second opening fluidly connected to said second lumen, (e) a first porous solid support for capturing carbohydrates provided in a solution of ≥95% organic solvent, said first porous solid support disposed between said first opening and said second opening and filling said area of said first cross section of said first lumen, said first porous solid support being (1) made of a non-hydrophilic material or having a surface of a non-hydrophilic material, or (2) made of a hydrophilic material or having a surface of a hydrophilic material, and (f) a second porous solid support, for capturing said reduced carbohydrates or carbohydrates labeled by reductive amination, said second porous solid support composed of a hydrophilic material, wherein said second porous solid support is disposed between said first porous solid support and said second opening and fills said area of said first cross section or of said second cross section,
(b) a reductant, or a label suitable for labeling carbohydrates by reductive amination, or both, and,
(c) instructions for reducing carbohydrates or for labeling carbohydrates by reductive amination, or both.

24. The kit of claim 23, further wherein said reaction container is a well in a multiwell plate, a tube, or a cartridge.

25. The kit of claim 24, wherein said reaction container is a well in a multiwell plate.

26. The kit of claim 25, wherein said second section of said well is a nozzle protruding from a bottom of said well.

27. The kit of claim 23, wherein said first porous solid support is polyethylene having pores or openings 10 microns or less in width.

28. The kit of claim 27, wherein said second porous solid support is composed of silica beads or particles covalently linked to a plurality of carbamoyl groups.

29. The kit of claim 28, wherein said reaction container is a well in a multiwell plate and further wherein said silica beads or particles covalently linked to a plurality of carbamoyl groups are disposed in a nozzle protruding from said bottom of said well.

30. The kit of claim 23, wherein said label is 2-aminobenzamide (2-AB), anthranilic acid (2-AA), 8-aminopyrene-1,3,6-trisulfonic acid (APTS), or procainamide hydrochloride.

31. The kit of claim 23, wherein said reductant is sodium cyanoborohydride or picoline borane, or both.

32. The kit of claim 23, further comprising one or more reagents for deglycosylating glycoconjugates.

33. The kit of claim 32, wherein said one or more reagents is a deglycosylation enzyme.

34. The kit of claim 33, wherein said deglycosylation enzyme is PNGase F.

* * * * *